United States Patent
Kara et al.

(10) Patent No.: US 6,537,779 B1
(45) Date of Patent: Mar. 25, 2003

(54) T7 PROMOTER-BASED EXPRESSION SYSTEM

(75) Inventors: Bhupendra Vallabh Kara, Macclesfield (GB); David Pioli, Macclesfield (GB); Kenneth Robert Bundell, Macclesfield (GB); Robert Craig Hockney, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/463,451

(22) PCT Filed: Jul. 21, 1998

(86) PCT No.: PCT/GB98/02175

§ 371 (c)(1),
(2), (4) Date: Apr. 3, 2000

(87) PCT Pub. No.: WO99/05297

PCT Pub. Date: Feb. 4, 1999

(30) Foreign Application Priority Data

Jul. 25, 1997 (GB) .............................. 9715660

(51) Int. Cl.⁷ .......................... C12N 15/00; C12N 1/20; C12N 15/09; C12P 21/06; C07H 21/04
(52) U.S. Cl. ................ 435/69.1; 435/320.1; 435/252.3; 435/471; 435/325; 435/455; 536/23.1; 536/24.1
(58) Field of Search .............................. 435/69.1, 320.1, 435/252.3, 325, 455, 471; 536/23.1, 24.1

(56) References Cited

FOREIGN PATENT DOCUMENTS

EP 0 502 637 A2 9/1992

OTHER PUBLICATIONS

Simons, et al. PNAS 81: 1624–1628, 1984.*
Dubendorff J W et al: " Controlling Basal Expression in an Inducible T7 Expression System by Blocking the Target T7 Promoter with LAC Repressor " Journal of Molecular Biology, vol. 219, No. 1, 1991, pp. 45–59 XP000605448 see the whole document.
Novagen: " pET Expression System Information Package " Aug. 1995 XP002084177 see the whole document.

* cited by examiner

Primary Examiner—Remy Yucel
Assistant Examiner—Gerald G. Leffers, Jr.
(74) Attorney, Agent, or Firm—Morgan, Lewis & Bockius LLP

(57) ABSTRACT

An improved T7 based promoter-driven protein expression system comprising an operator sequence downstream of the T7 promoter sequence, and having a further operator sequence upstream of the T7 promoter sequence.

12 Claims, 16 Drawing Sheets

TNF accm (max) % TMP

T7 PROMOTER-BASED EXPRESSION SYSTEM

This application is the national phase of international application PCT/GB98/02175 filed Jul. 21, 1998 which designated the U.S.

The invention relates to expression systems for the recombinant synthesis of polypeptides, in particular to T7 promoter-driven protein expression systems. The invention also relates to expression vectors for use in such systems.

A large number of mammalian, yeast and bacterial host expression systems are known (Methods in Enzymology (1990), 185, Editor: D. V. Goeddel). Of particular interest are those which use T7 RNA polymerase. The ability of T7 RNA polymerase and equivalent RNA polymerases from T7-like phages to transcribe selectively any DNA that is linked to an appropriate promoter can serve as the basis for a very specific and efficient production of desired RNAs both in vitro and inside a cell.

U.S. Pat. No. 4952496 (Studier) discloses a process whereby T7 RNA polymerase can be expressed and used to direct the production of specific proteins, all within a host *E. coli* cell. Specific proteins of interest include antigens for vaccines, hormones, enzymes, or other proteins of medical or commercial value. Potentially, the selectivity and efficiency of the phage RNA polymerase could make such production very efficient. Furthermore, the unique properties of these phage RNA polymerases may make it possible for them to direct efficient expression of genes that are expressed only inefficiently or not at all by other RNA polymerases. These phage polymerases have the further advantage that it is possible to selectively inhibit the host cell RNA polymerase so that all transcription in the cell will be due to the phage RNA polymerase.

An expression system based on the above is now commercially available. This is the pET system obtainable from Novagen Inc. 597 Science Drive, Madison, WI 53711. This system is suitable for the cloning and expression of recombinant proteins in *E. coli*. See also Moffat et al, J. Mol. Biol., 1986, 189, 113–130; Rosenberg et al, Gene, 56, 125–135; and Studier et al, Meth. Enzymol. 1990, 185, 60–89.

However, despite the provision of the pET system, there remains the need for further, improved T7 promoter-driven expression systems.

We have now devised such a system which provides improved control of expression and improved levels of protein expression, when compared to available 17-based expression systems. We provide a T7 promoter-driven expression system wherein basal expression in the absence of inducer is reduced to a level which permits the cloning and expression of toxic gene products not possible with currently available T7 based expression systems whilst not influencing induced productivity. Moreover, our present invention also allows control of production of heterologous proteins in an inducer concentration-dependent manner over a wide range of expression levels so that an optimum level of expression can be identified. This level of control over expression and production of heterologous protein is not possible with currently available T7 based expression systems.

Therefore in a first aspect of the invention we provide a T7 promoter-driven protein expression system comprising an operator sequence downstream of the T7 promoter sequence, and having a further operator sequence upstream of the T7 promoter sequence.

We have found that the further operator is preferably a native lac operator (lacO) sequence. Or a perfect palindrome operator (ppop) sequence. More preferably the native (lac) operator sequence downstream of the T7 promoter sequence is replaced by a ppop sequence, so as to provide a tandem ppop operator.

The T7 promoter driven expression system is conveniently constructed as follows- The target gene of interest is cloned in a plasmid under control of bacteriophage transcription and translation signals. The target gene is initially cloned using a host such as *E.coli* DH5α, HB101 that does not contain the T7 RNA polymerase gene. Once established, plasmids are transferred into expression hosts containing a chromosomal copy of the T7 RNA polymerase gene under for example lac UV5 control. Other convenient promoters include lac, trp, tac, trc, and bacteriophage λ promoters such as pL and pR. Expression is then induced by the addition of an inducer such as IPTG (isopropyl-β-D-1-thiogalactopyranoside), lactose or melibiose. Other inducers may be used and are described more fully elsewhere. See The Operon, eds Miller and Reznikoff (1978). Inducers may be used individually or in combination.

The plasmid preferably includes one or more of the following: a selectable antibiotic resistance sequence, a cer stability element, and a multiple cloning site. The construction of appropriate plasmids will be apparent to the scientist of ordinary skill. Examples of preferred plasmids comprising one or more of the above features are illustrated by the pZT7#3-series of plasmids in the accompanying Figures. These were constructed starting from a vector pZEN0042 disclosed (as pICI0042) in our European Patent Application No. 0 502 637 (ICI). The 3-series plasmids of this invention include pZT7#3.0, pZT7#3.1, pZT7#3.2 and pZT7#3.3. A particularly preferred plasmid of this invention is the pZT7#3.3 plasmid.

The chromosomal copy of the T7 RNA polymerase gene, for example under lac UV5 control, is preferably introduced into the host cells via the λ bacteriophage construct, λDE3, obtainable from Novagen. The T7 RNA polymerase expression cassette may also be delivered to the cell by infection with a specialised bacteriophage λ transducing phage that carries the gene (CE6, U.S. Pat. No. 4,952, 496.

Compatible plasmids such as pLysS and pLysE (also available from Novagen) may also be introduced into the expression host. These plasmids encode T7 lysozyme, which is a natural and selective inhibitor of T7 RNA polymerase, and thus reduces its ability to transcribe target genes in uninduced cells. pLysS hosts produce low amounts of T7 lysozyme, while pLysE hosts produce much more enzyme and therefore provide more stringent control.

Any convenient compatible prokaryotic or eukaryotic host cell may be used. The most commonly used prokaryotic hosts are strains of *E.coli*, although other prokaryotic hosts such as *Salmonella typhimurium, Serratia marsescens, Bacillus subtilis* or *Pseudomonas aeruginosa* may also be used. Mammalian (e.g. Chinese hamster ovary cells) or other eukaryotic host cells such as those of yeast (e.g. *Saccharomyces cerevisiae, Pichia pastoris, Hansenula polymorpha, Schizosaccharomyces poinbe* or *Kluyveroromyces lactis*), filamentous fungi, plant, insect, amphibian or ovarian species may also be useful. A particular host organism is a bacterium, preferably *E. coli* (e.g. K12 or B strains).

Any convenient growth medium may be used depending on the host organism used. For *E.coli*, practice of this invention includes, but is not limited to complex growth media such as L-broth or minimal growth media such as M9 (described hereinafter).

The invention will now be illustrated but not limited by reference to the following detailed description Examples, Tables and Figures wherein:

Table 1 gives details of plasmids expressing h-TNFα used in the Examples. Tables 2–4 gives details of vectors used in the Examples and their relative performance.

Table 5 gives details of the composition of M9 minimal growth medium.

Table 6 gives details of h-TNFα expression in various growth media.

Table 7 gives details of host/transformation efficiencies for vectors used in the Examples.

Table 8 gives details of DNase 1 productivity in conjunction with the pZT7#3.3:DNase 1 vector.

Tables 9–11 give details of accumulation levels for LAR d1 (aa1275–1623), ZAP70 (4–260) 6HIS and MCP-1 {9–76} used in the Examples.

Table 12 shows the sequences of oligonucleotides used in the construction of pZT7#3.3 and intermediate vectors.

Table 13 shows the nucleic acid sequence of hTNFα.

Table 14 shows the ZAP70 (4–260) 6HIS nucleic acid sequence.

Table 15 shows the LAR d1 (aa1275–1623) nucleic acid sequence.

Table 16 shows the bovine pancreatic DNase 1 nucleic acid sequence.

Table 17 shows the human carboxypeptidase B (mutant D253>K) 6His cmyc sequence.

Table 18 shows various *E. coli* expression strains.

Table 19 shows the human monocyte chemotactic protein MCP-1 {9–76} sequence.

Table 20 shows the A5B7 F(ab')$_2$ nucleic acid sequence.

SPECIFIC DESCRIPTION

1. Generation of pZT7 Series Vectors

Figure 1:
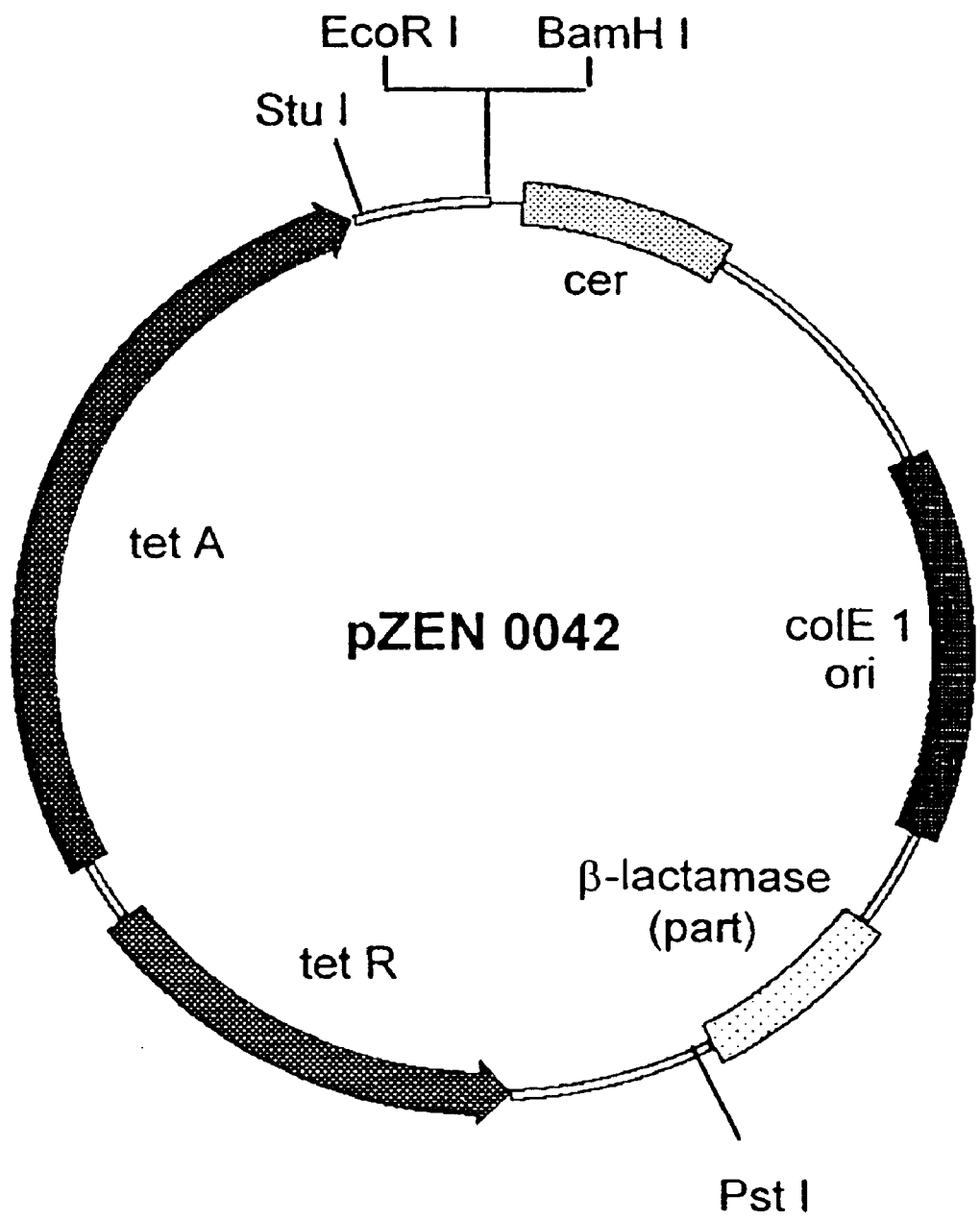
FIG. 1 shows the pZEN0042 plasmid.

The starting vector for generation of pZT7#3.3 was pZEN0042, described fully in our European Patent Application, Publication No. 0502637. Briefly, this vector contains the tetA/tetR inducible tetracycline resistance sequence from plasmid RP4 and the cer stability sequence from plasmid pKS492 in a pAT153 derived background (FIG. 1).

1(i) Cloning of lac I

The sequence of lac I including the lac repressor coding sequence and lac I promoter was generated by polymerase chain reaction using genomic DNA prepared from *E.coli* strain MSD 101 (W3110). Nsi I restriction endonuclease sites were generated at both ends of the sequence by incorporation into the PCR primers #1 and.

Figure 2:
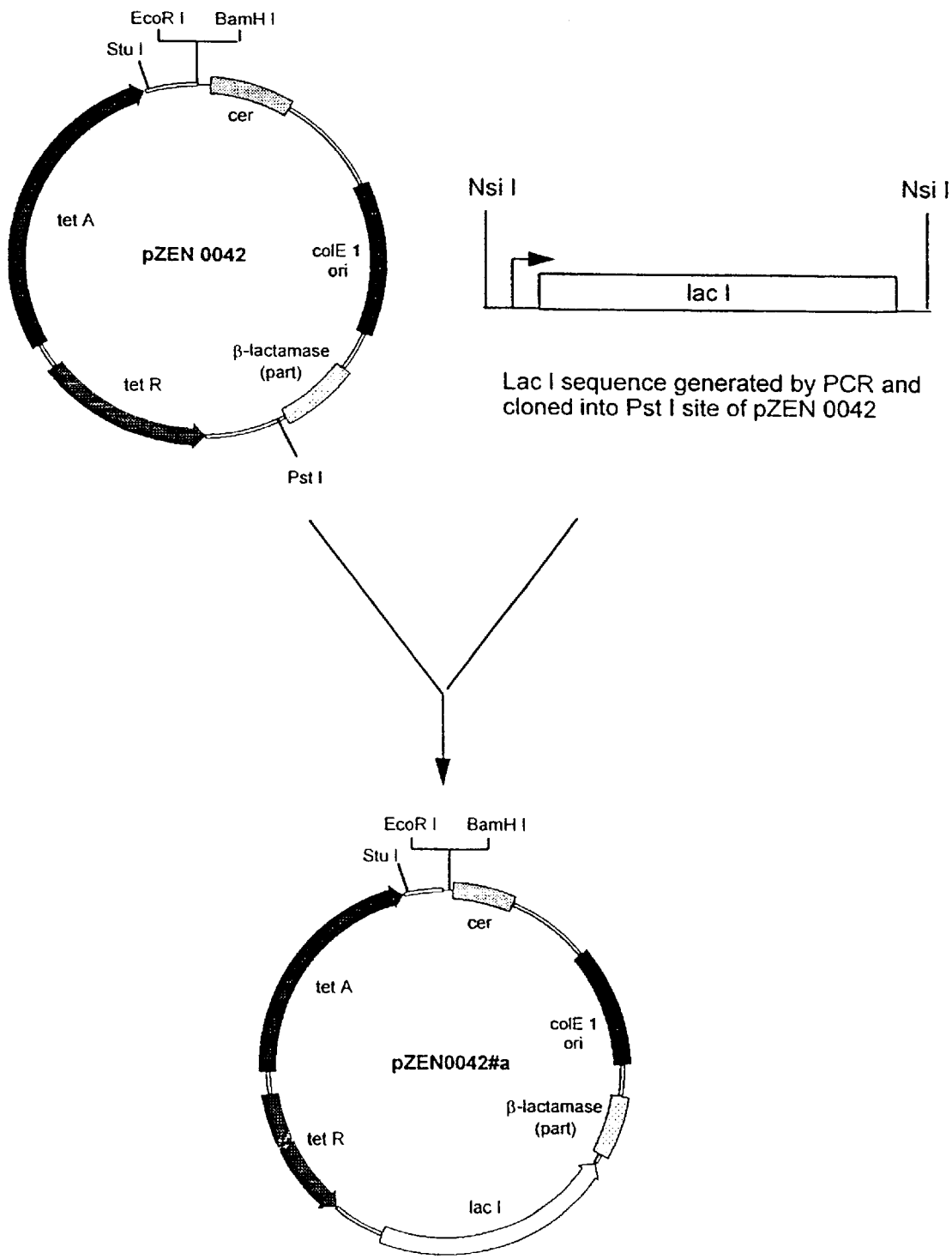
FIG. 2 shows the construction of pZEN0042#a from pZEN0042.

2 (Table 12). The PCR product obtained was digested with Nsi I and cloned into pZEN0042 at the Pst I site (Pst I and Nsi I have compatible cohesive ends resulting in both sites being destroyed). Both orientations of lac I were obtained. A clone with a correct sequence lac I in the anti-clockwise orientation was identified (=pZEN0042#a) (FIG. 2).

1(ii) Cloning of Polylinker

A new multiple cloning site was generated in pZEN0042#a to allow subsequent cloning of the T7 expression cassette. This was achieved by digesting pZEN0042#a with EcoR I and BamH I and ligating with annealed, synthetic oligomers #3 and #4 (Table 12).

Figure 3:
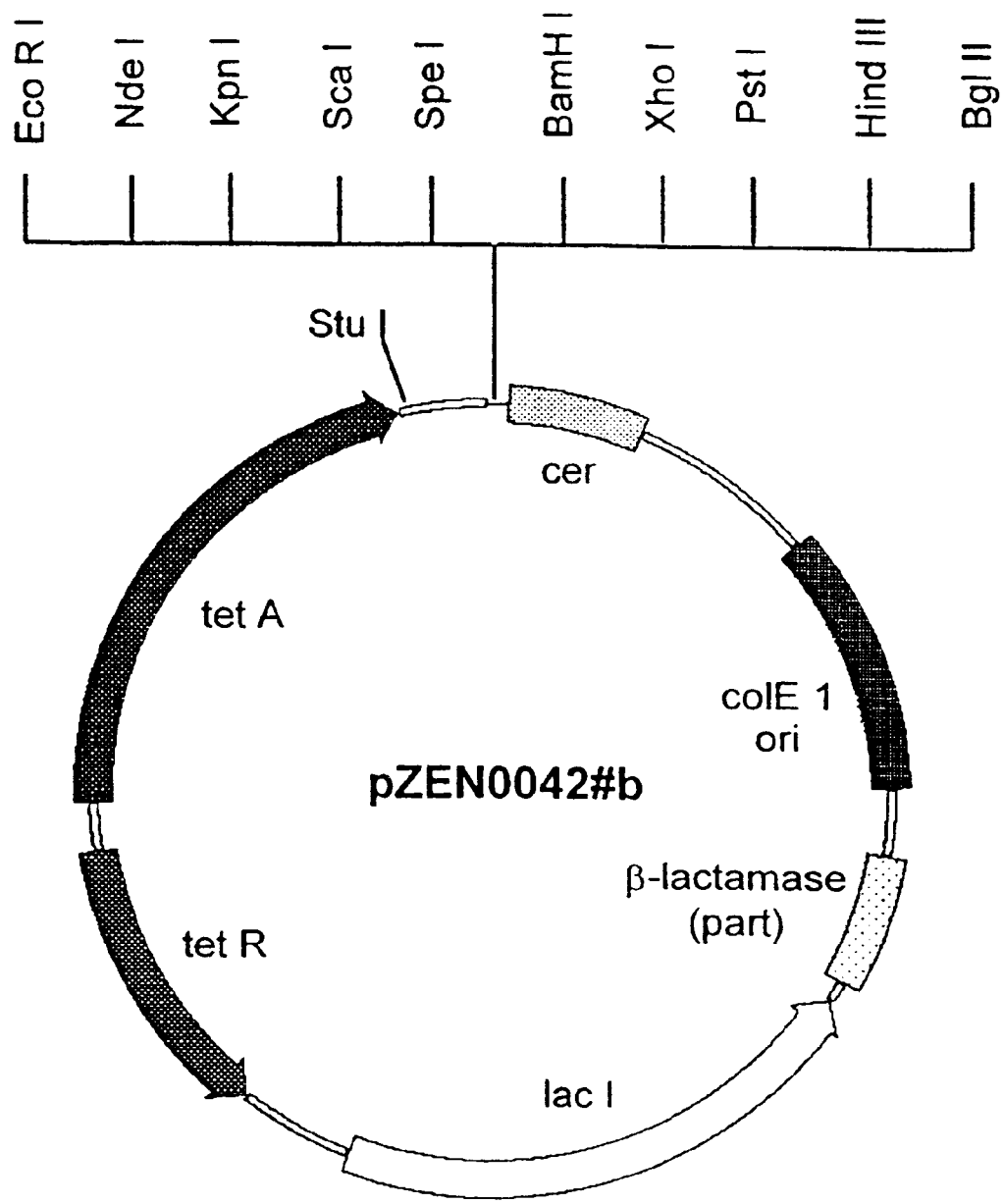
FIG. 3 shows the pZEN0042#b plasmid.

The polylinker of the resulting vector, pZEN0042#b, had the following restriction sites: EcoRI-Nde I-Kpn I-Sca I-Spe I-BamH I-Xho I-Pst I-Hind III-Bgl II.

pZEN0042#b is shown in FIG. 3.

Cloning of T7 Expression Elements

2(i) T7 Terminator

Figure 4:
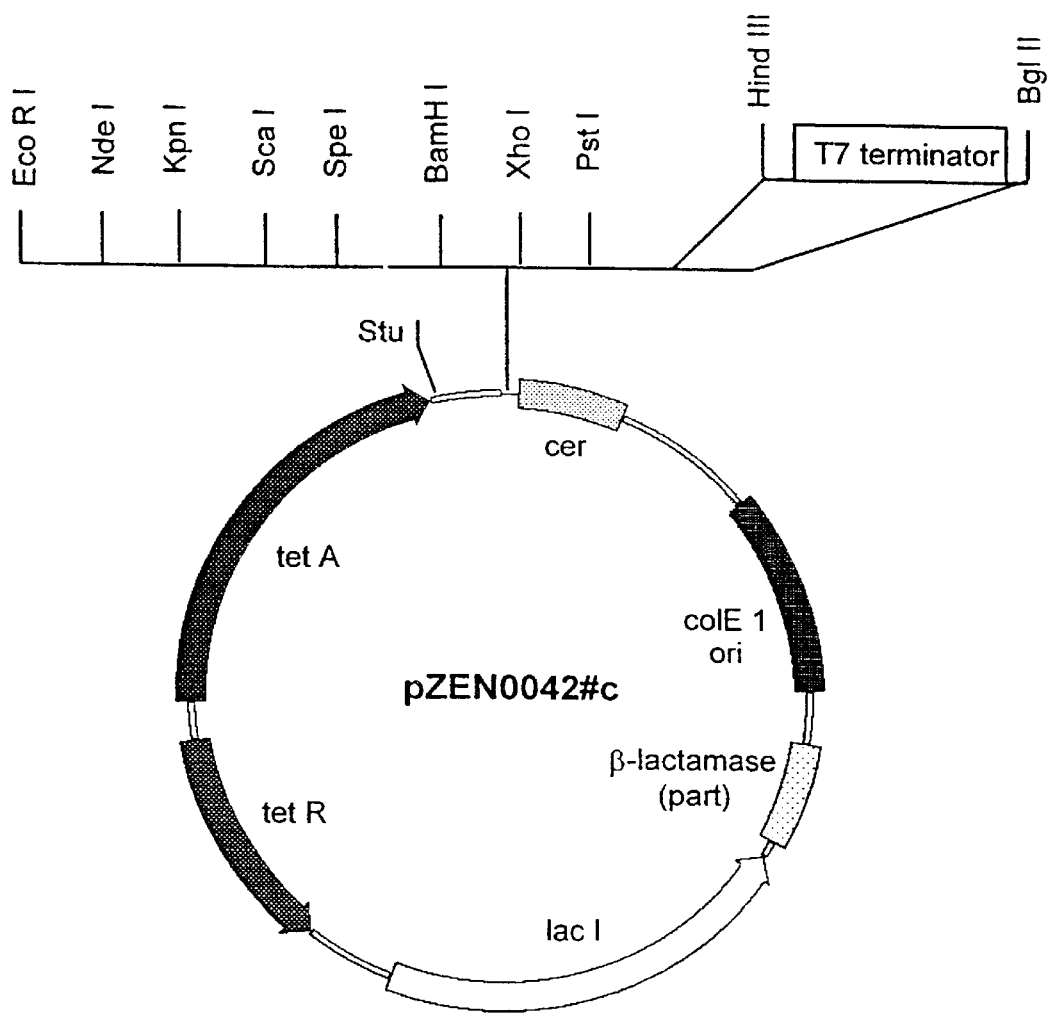
FIG. 4 shows the pZEN0042#c plasmid.

The T7 terminator sequence from T7 gene 10 was cloned as annealed synthetic oligomers #5 and #6 (Table 12) between the Hind III and Bgl II sites of pZEN0042#b to generate ZEN0042#c (FIG. 4).

2(ii) tRNA$^{arg5}$

Figure 5:
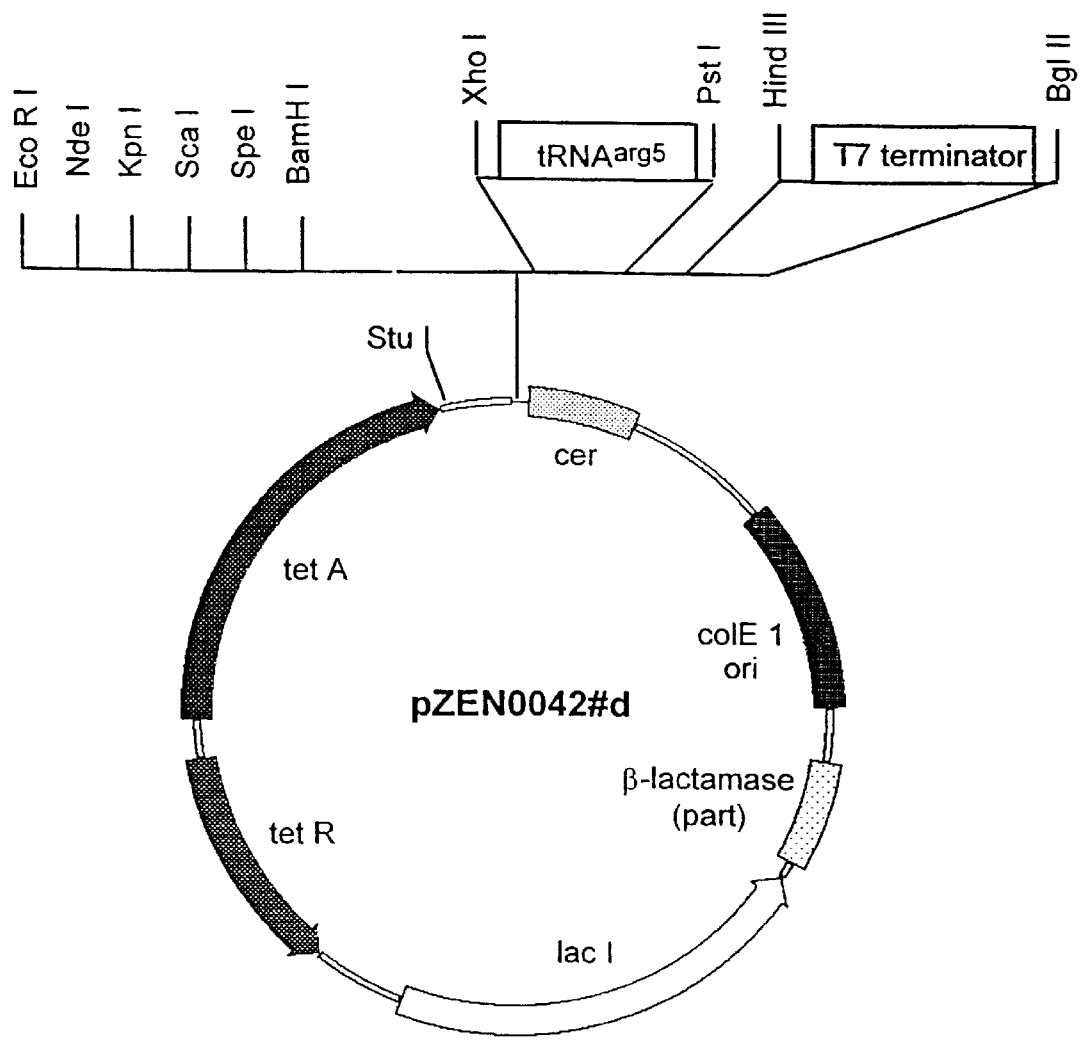
FIG. 5 shows the pZEN0042#d plasmid.

The tRNA$^{arg5}$ transcriptional reporter sequence (Lopez, et al, (1994), NAR 22, 1186–193, and NAR 22, 2434) was cloned as annealed synthetic oligomers #7 and #8 (Table 12) tween the Xho I and Pst I sites in pZEN0042#c to generate pZEN0042#d (FIG. 5).

2(iii) Upstream Terminator

Figure 6:
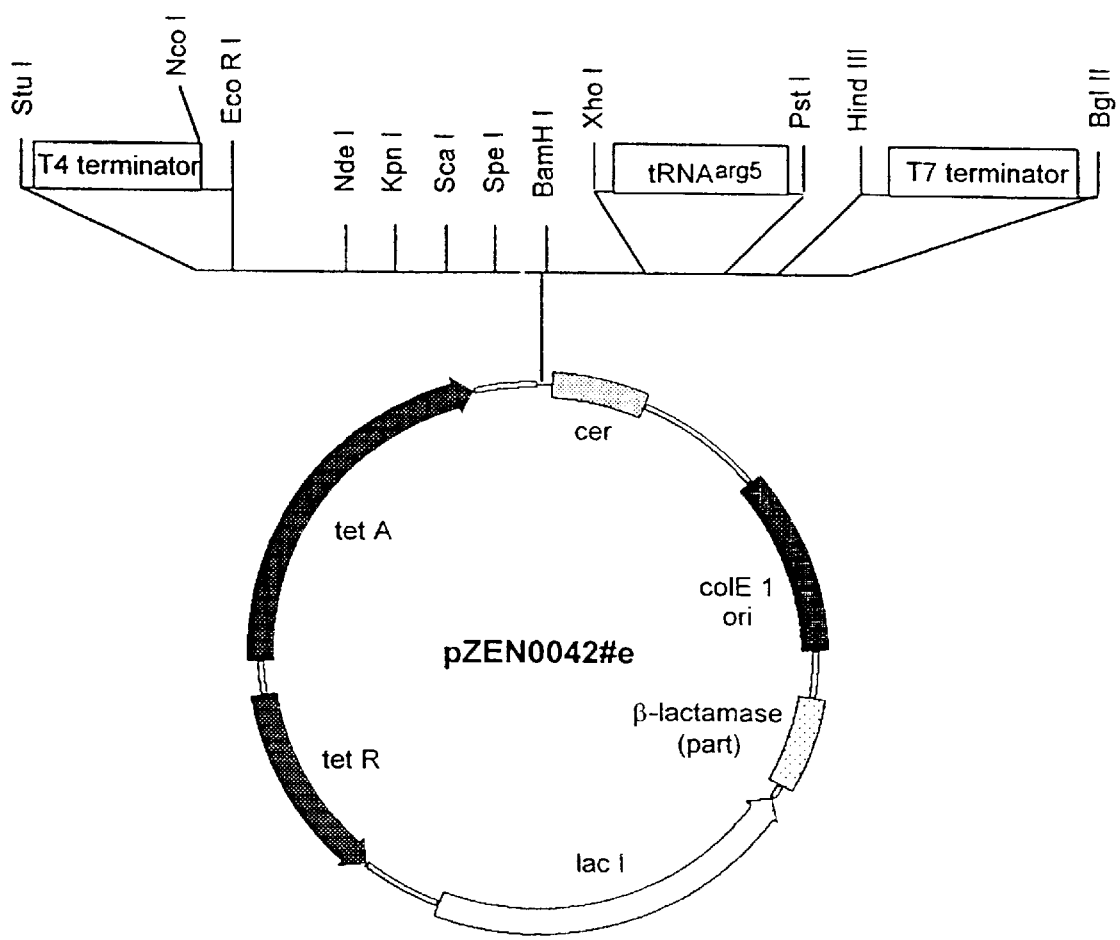
FIG. 6 shows the pZEN0042#e plasmid.

As the tetA sequence has no recognisable terminator, a T4 terminator sequence was cloned upstream of the EcoR I site to reduce potential transcriptional readthrough from tetA (or any other unidentified promoter sequence) into the T7 expression cassette (to be cloned downstrem of the EcoR I site). Annealed synthetic oligomers #9 and #10 (Table 12) containing the T4 terminator sequence and an additional Nco I site were cloned between the Stu I and EcoR I sites in pZEN0042#d to generate pZEN0042#e (FIG. 6).

2(iv) T7 lac Promoter

Figure 7:
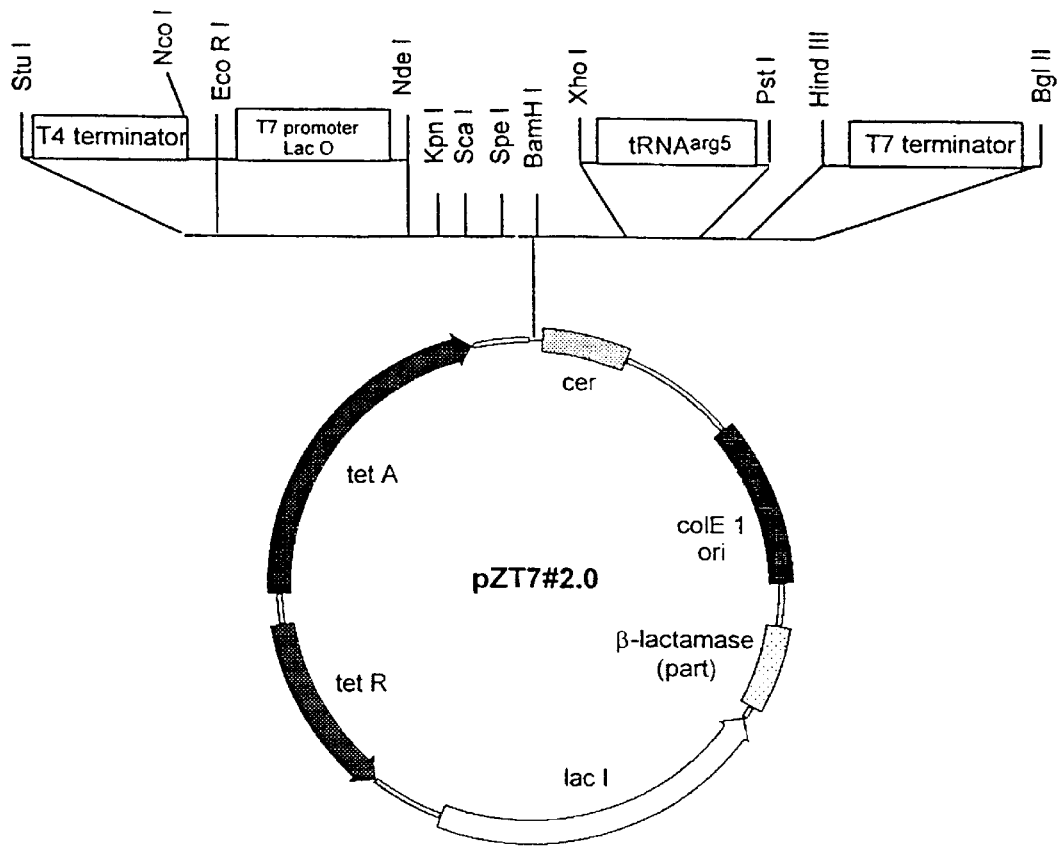
FIG. 7 shows the pZT7#2.0 plasmid.

The T7 promoter and lac operator sequence was cloned as annealed synthetic oligonucleotides #11 and #12 (Table 12) between the EcoR I and Nde I sites of pZEN0042#e to generate pZT7#2.0 (FIG. 7). This configuration of T7 promoter and lac operator is equivalent to pET11a.

2(v) T7 Promoter with Perfect Palindrome Operator

Figure 8:
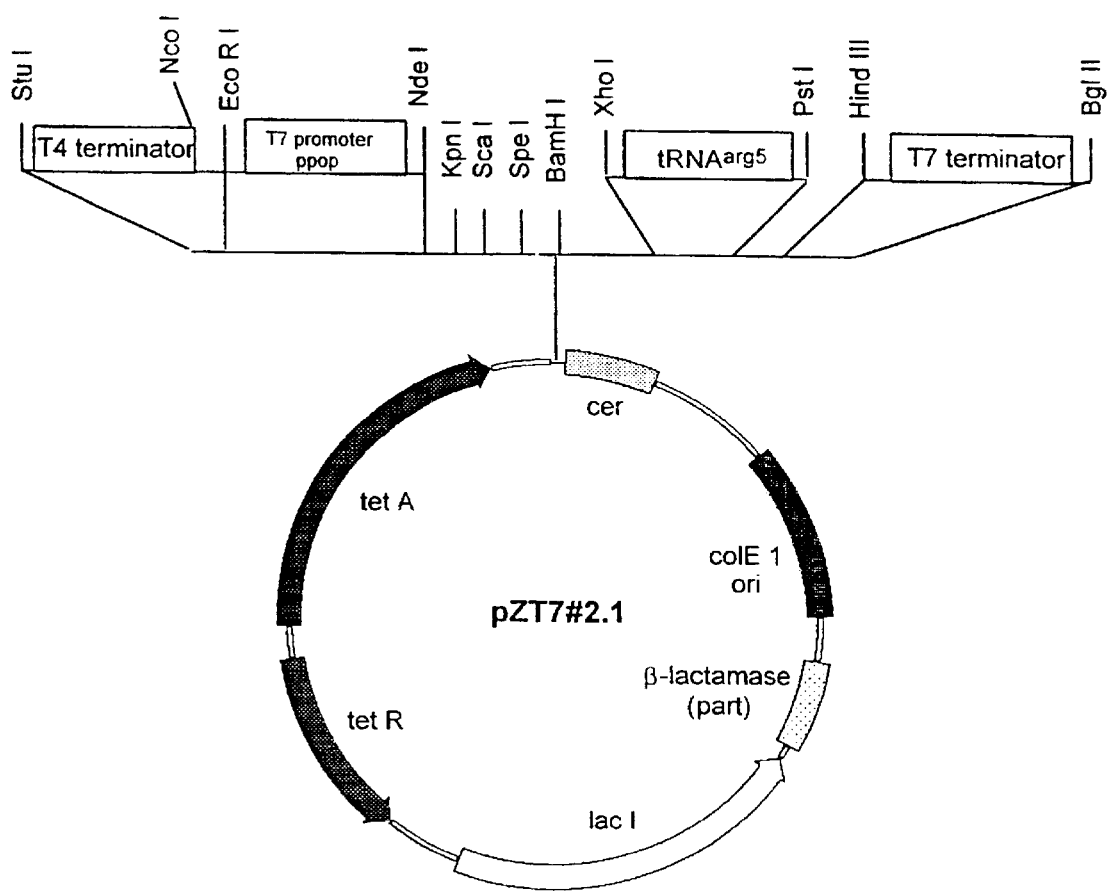
FIG. 8 shows the pZT7#2.1 plasmid.

The T7 gene 10 promoter incorporating a perfect palindrome lac operator sequence (Simons et al (1984), PNAS 81,1624–1628) was cloned as annealed synthetic oligomers #13 and #14 (Table 12) between the EcoR I and Nde I sites of pZEN0042#e to generate pZT7#2.1 (FIG. 8).

2(vi) Upstream lac Operator

Figure 9:
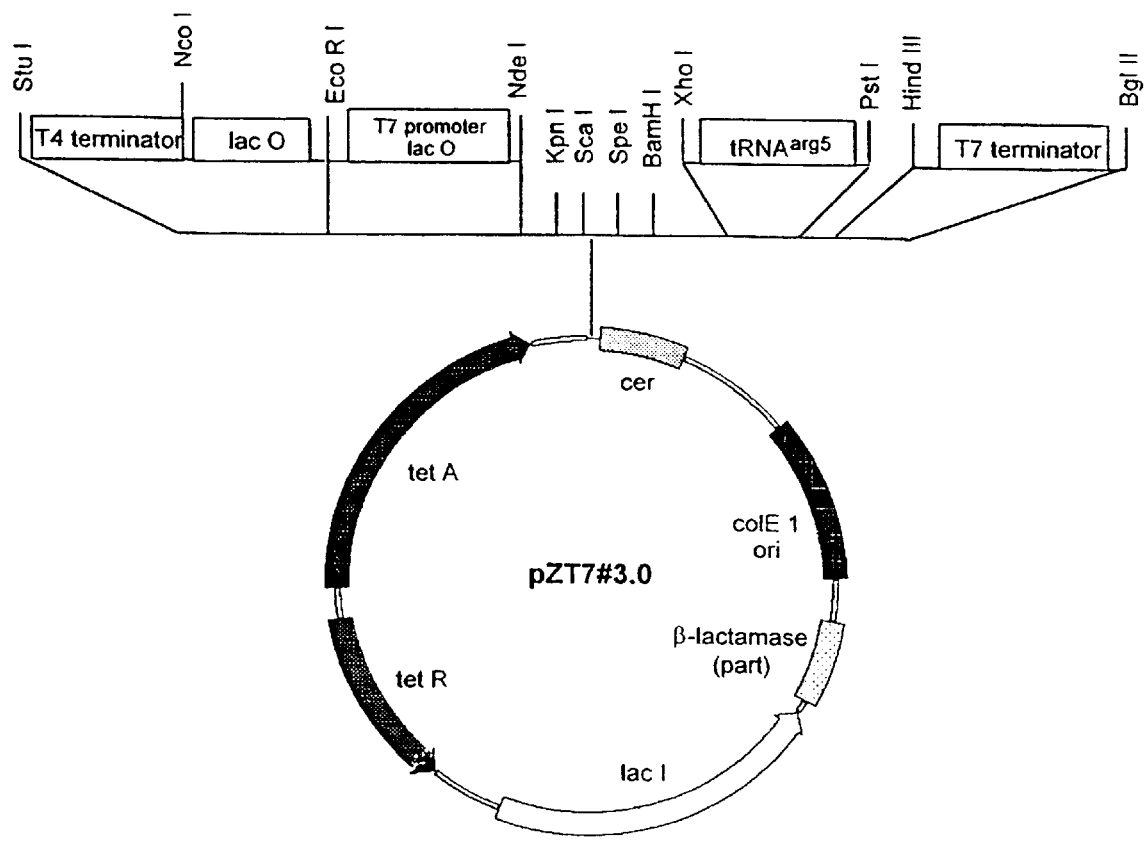
FIG. 9 shows the pZT7#3.0 plasmid of the invention.

A second native lac operator sequence was cloned 94 base pairs upstream of the lac operator sequence in pT7#2.0 as annealed synthetic oligomers #15 and #16 (Table 12) between the Nco I and EcoR I sites of pZT7#2.0 to generate pZT7#3.0 (FIG. 9).

Figure 10:
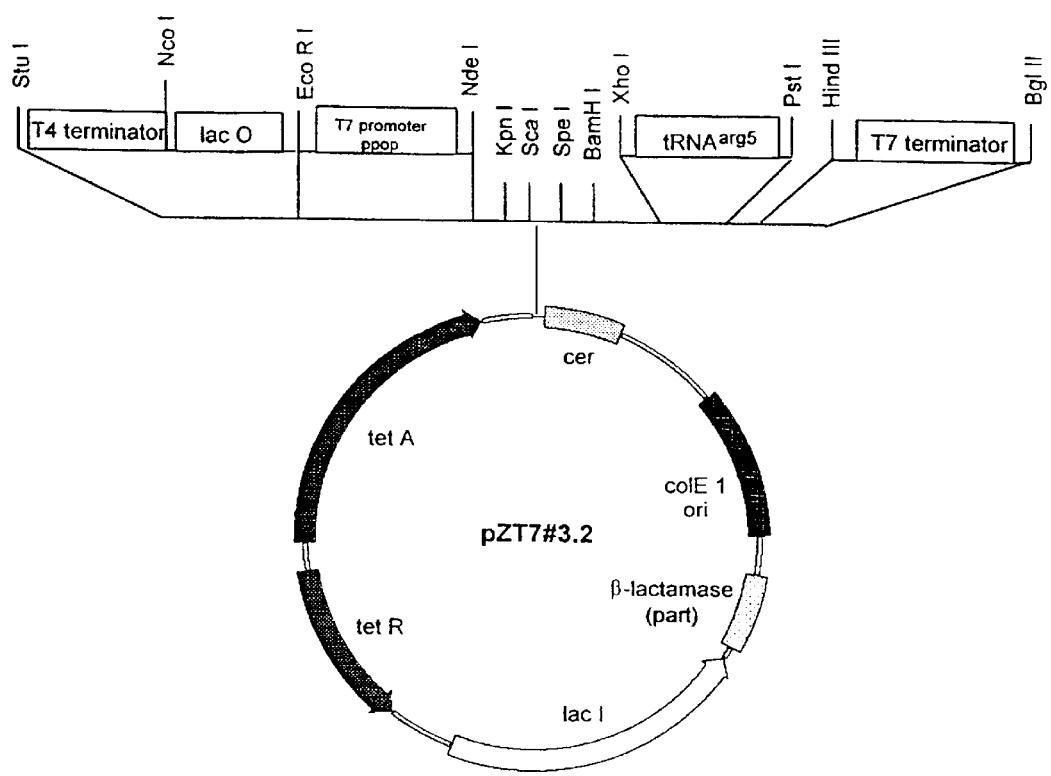
FIG. 10 shows the pZT7#3.2 plasmid of the invention.

The same lac operator sequence was cloned similarly into pZT7#2.1 to generate pZT7#3.2 (FIG. 10).

2(vii) Upstream Perfect Palindrome lac Operator

Figure 11:
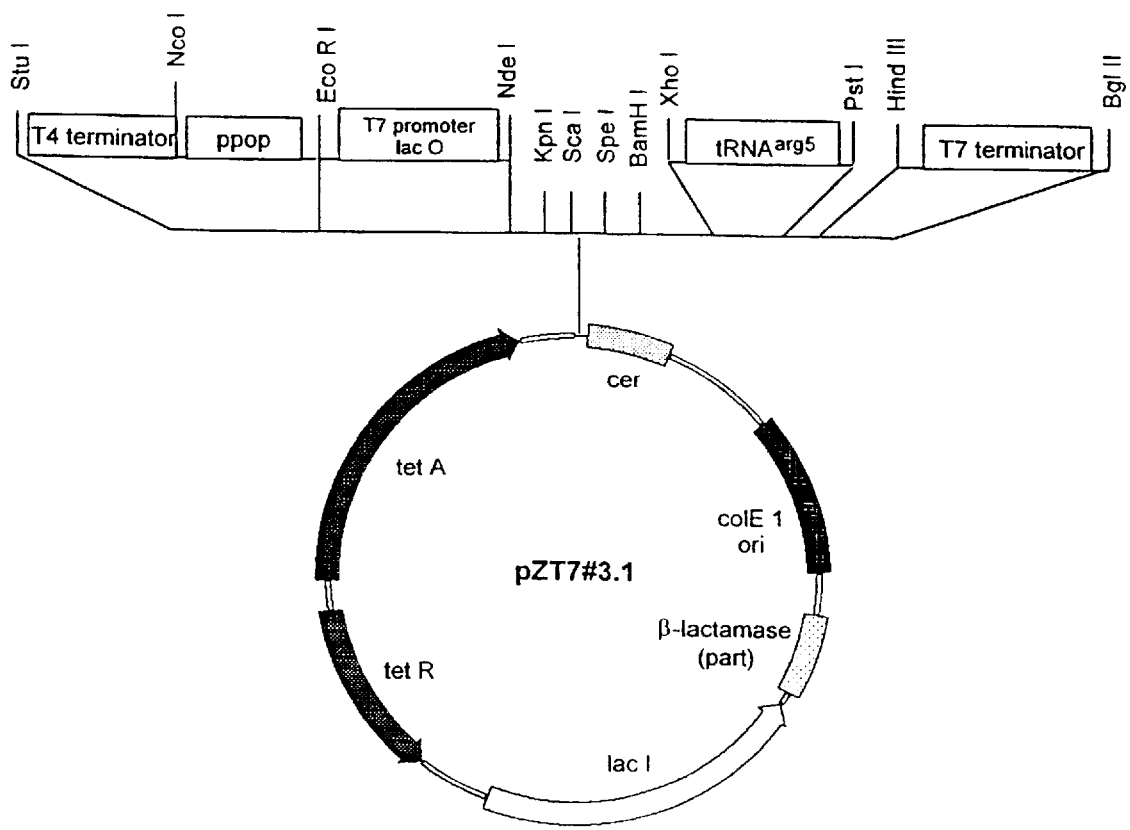
FIG. 11 shows the pZT7#3.1 plasmid of the invention.

A perfect palindrome operator sequence was positioned 94 bp upstream of the lac operator sequence of pZT7#2.0 by cloning of annealed synthetic oligomers #17 and #18 (Table 12) between the Nco I and EcoR I sites of pZT7#2.0 to generate pZT7#3.1 (FIG. 11).

Figure 12:
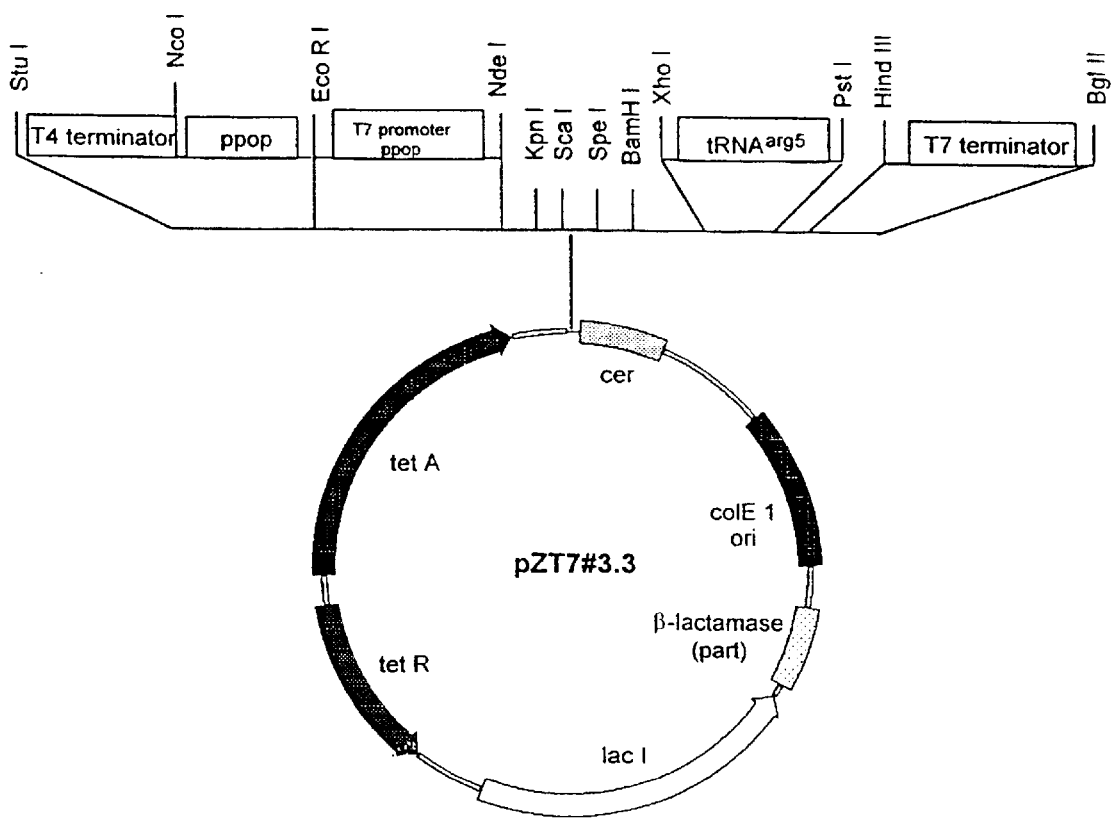
FIG. 12 shows the pZT7#3.3 plasmid of the invention.

The same perfect palindrome operator sequence was cloned similarly into pZT7#2.1 to generate pZT7#3.3 (FIG. 12).

3. Generation of Test Constructs pET11a

T7 expression vector pET11a was obtained from Novagen Inc and used as a control for the testing of the pZT7 vectors 3(i) hTNFα

An Nde I-BamH I DNA fragment containing the coding sequence of human TNFα was cloned between the Nde I and BamH I sites in vectors pZT7#2.0, pZT7#2.1, pZT7#3.0, pZT7#3.1, pZT7#3.2, pZT7#3.3 and pET11a. The sequence cloned is shown in Table 13

3(ii) ZAP70 (4–260) 6HIS

A DNA fragment encoding amino acids 4–260 of human protein tyrosine kinase ZAP70 with a C-terminal hexahistidine tag sequence was subcloned as a Nde I-Bgl II fragment between the Nde I and BamH I cloning sites of pET11a and pZTF7#3.3. The sequence cloned is shown in Table 14.

3(iii) LAR d1 (aa1275–1623)

The leukocyte antigen related protein tyrosine phosphatase domain 1 (aa1275–1613) was subcloned as a Nde I-Bgl II fragment into pET11a and pZT7#3.3 (Nde I-BamH I). The sequence cloned is shown in Table 15.

3(iv) Human Carboxypeptidase B (Mutant D253>K) 6His cmyc

The coding sequence of a mutant human carboxypeptidase (D253>K) with a C-terminal hexahistidine cmyc tag sequence was placed downstream of the Erwinia carotovora pel B secretory leader sequence and cloned into pZT7#3.3 and pET11a. The sequence cloned is shown in Table 17

3(v) Bovine Pancreatic DNase 1

The coding sequence of bovine pancreatic DNase I was cloned as an Nde I-Bgl II fragment between the Nde I and BamH I sites in pZT7#3.3. The sequence cloned is shown in Table 16.

This sequence could not be cloned without mutation in pET11a.

However, a bovine pancreatic DNase 1 sequence had previously been cloned into pET11 (not pET11a) (Doherty et al (1993) Gene, 136, pp337–340). In this construct the 5' untranslated region including the ribosome binding site is derived from the native bovine pancreatic DNase 1 sequence rather than from T7 gene 10 as in pT7#3.3. This construct, pAD10, was used as a control for pT7#3.3.

3(vi) Human Monocyte Chemotactic Protein MCP-1 {aa9–76}

The coding sequence of human monocyte chemotactic protein (aa9–76) was cloned between the Nde I and BamH I sites of pZT7#3.3 and pET11a. The sequence cloned is shown in Table 19.

3(vii) A5B7 F(ab')$_2$

The coding sequence of A5B7 F(ab')$_2$ was placed downstream of the Erwinia carotovora pel B secretory leader sequence and cloned between the Nde I and BamH I sites of pZT7#3.3 and pET11a. The sequence cloned is shown in Table 20.

4. Generation of Host Strains for T7 Expression

A λDE3 lysogenisation kit was obtained from Novagen Inc and used according to the instructions to generate T7 expression hosts from the E.coli strains listed in Table 18.

Plasmids pLysS and pLysE and E.coli expression hosts BL21 and BL21(DE3) were obtained from Novagen Inc.

EXAMPLE 1

E.coli strains BL21(DE3), BL21(DE3) pLysS, BL21 (DE3) pLysE were transformed separately with plasmids (described below, Table 1) expressing human TNFα. The resultant recombinant strains were purified and maintained in glycerol stocks at −80° C. Host strains BL21(DE3), BL21(DE3) pLysS and BL21(DE3)pLysE are used extensively in the art and are freely available to the public, for example, from Novagen Inc (Madison, USA). The genotype of BL21(DE3) is F−, ompT, hsdS$_B$(r$_B^-$m$_B^-$), gal, dcm, (DE3).

TABLE I

| Host | Plasmid | Description | Recombinant Designation No |
|---|---|---|---|
| BL21(DE3) | pZen1798 | pET11a:TNFα | BL21(DE3) pZen1798 |
| BL21(DE3) | pZen1830 | pZT7#2.0:TNFα | BL21(DE3) pZen1830 |
| BL21(DE3) | pZen1832 | pZT7#2.1:TNFα | BL21(DE3) pZen1832 |
| BL21(DE3) | pZen1835 | pZT7#3.0:TNFα | BL21(DE3) pZen1835 |
| BL21(DE3) | pZen1836 | pZ17#3.1:TNFα | BL21(DE3) pZen1836 |
| BL21(DE3) | pZen1826 | pZT7#3.2:TNFα | BL21(DE3) pZen1826 |
| BL21(DE3) | pZen1827 | pZT7#3.3:TNFα | BL21(DE3) pZen1827 |
| BL21(DE3) pLysS | pZen1798 | pET11a:TNFα | BL21(DE3) pLysS/pZen1798 |
| BL21(DE3) pLysE | pZen1798 | pET11a:TNFα | BL21(DE3) pLysE/pZen1798 |
| BL21(DE3) pLysS | pZen1830 | pZT7#2.0:TNFα | BL21(DE3) pLysS/pZen1830 |
| BL21(DE3) pLysE | pZen1830 | pZT7#2.0:TNFα | BL21(DE3) pLysE/pZen1830 |

An aliquot of each recombinant strain was removed from stock and streaked onto L-agar plates (supplemented with ampicillin (50 µg/ml) or tetracycline (10 µg/ml) and/or chloramphenicol (1 µg/ml) to maintain selection as appropriate) and incubated at 37° C. for 16 hours. An aliquot of each culture was then resuspended in 10 ml of sterile PBS (phosphate buffered saline solution; 8 g/L sodium chloride, 0.2 g/L potassium chloride, 0.2 g/L potassium di-hydrogen orthophosphate, 1.15 g/L magnesium chloride) and used to inoculate to OD$_{550}$=0.1 each of two 250 ml Erlenmeyer flasks containing 75 ml of L-broth (10 g/L tryptone (Difco), 5 g/L yeast extract (Difco), 5 g/L sodium chloride; pH 7.2) supplemented with tetracycline (10 µg/ml) or ampicillin (50 µg/ml) and/or chloramphenicol (1 µg/ml) as appropriate. The flasks were then incubated at 37° C. on a reciprocating shaker. Growth was monitored until OD$_{550}$=0.4–0.5. At this point cultures were induced by adding the inducer, IPTG (isopropyl-β-D-1-thiogalactopyranoside), to a final concentration of 1 mM to one flask from each set (of two) for each recombinant strain. The second flask was not induced. Both flasks for each recombinant strain were incubated under the conditions described above for a further 24 h. The accumulation level of hTNFα in the induced cultures was determined by laser densitometry scanning of Coomassie blue stained gels following SDS-PAGE of the sampled bacteria. The basal accumulation level of hTNFα in the un-induced cultures was determined by Western blot analysis (using an anti-hTNFα antibody) following SDS-PAGE of the sampled bacteria. The accumulation level in terms of molecules of hTNFα per cell was then determined by laser densitometry scanning of the blots (prepared using known standards together with the "unknowns") as is well established in the art. The results are summarised below (Table 2).

TABLE 2 hTNFα: Accumulation level: Basal and Induced

| VECTOR | Operator[1] | Basal % TMP[2] | Basal mol/cell[3] | Induced % TMP[2] |
|---|---|---|---|---|
| pET11a | single native lacO | 3.06 | 98000 | 30 |
| pZT7#2.0 | single native lacO | 2.66 | 85000 | 33 |
| pZT7#3.0 | dual native lacO | 0.14 | 4500 | 31 |
| pZT7#2.1 | single ppop lacO | 1.22 | 39000 | 33 |
| pZT7#3.1 | dual ppop/native lacO | 0.59 | 19000 | 37 |
| pZT7#3.2 | dual native/ppop lacO | 0.08 | 2400 | 39 |
| pZT7#3.3 | dual ppop lacO | 0.016 | 500 | 44 |
| pET11a/pLysS | single native lacO | 0.045 | 1400 | 2.2 |
| pET11a/pLysE | single native lacO | 0.025 | 800 | 0.21 |
| pZT7#2.0/pLysS | single native lacO | 0.02 | 600 | 1.2 |
| pZT7#2.0/pLysE | single native lacO | nd[4] | nd[4] | 0.15 |

[1]described more fully in the text
[2]TMP = Total Microbial Protein
[3]mol/cell = molecules of hTNFα per cell; detection limit: 250 molecules/cell
[4]nd = not detected (Western blot)

The data presented above clearly shows that the level of basal expression of a heterologous protein is still high using the current established art (single native lac operator: vectors pET11a/pZT7#2.0). Basal expression can be reduced with pET11a/pZT7#2.0 expression systems by use of host strains co-transformed with plasmids expressing T7 lysozyme (pLysS/pLysE). However, the induced productivity is severely compromised.

Surprisingly, the dual native lac operator sequence works with a T7 promoter driven system reducing basal expression levels significantly whilst not influencing induced productivity.

More surprisingly, the dual perfect palindrome operator performs the best in reducing basal expression levels yet further without compromising induced productivity. This is totally unexpected given that the use of a single perfect palindrome operator with a T7 promoter driven system does not yield a significant improvement in reducing basal expression. Other combinations of the native and ppop lac operators may also be used e.g. pZT7#3.2 and pZT7#3.1.

EXAMPLE 2

E.coli strains MSD 623(DE3), MSD 624(DE3), MSD 68(DE3), MSD 101(DE3) and MSD 522(DE3)—see Table 18, were transformed separately with plasmids pET11a:TNF, pZT7#2.0:TNF, pZT7#2.1:TNF, pZT7#3.0:TNF, pZT7#3.1:TNF, pZT7#3.2:TNF and pZT7#3.3:TNF expressing human TNFα (described previously (Table 1)). The resultant recombinant strains were purified and maintained in glycerol stocks at −80° C. The level of basal and induced expression/accumulation of hTNFα was determined exactly as described in Example 1. The basal (un-induced) and IPTG induced level of hTNFα expression/accumulation are summarised below in Table 3 and 4 respectively. The data obtained using host strain BL21(DE3), described in Example 1, is included for reference.

TABLE 3

Host Strain/Basal hTNFα accumulation level: molecules per cell*

| VECTOR | BL21 (DE3) | MSD623 (DE3) | MSD624 (DE3) | MSD68 (DE3) | MSD101 (DE3) | MSD522 (DE3) |
|---|---|---|---|---|---|---|
| pET11a | 98000 | 7600 | 4200 | 2300 | 4300 | 6500 |
| pZT7#2.0 | 85000 | 7000 | 2800 | 3000 | 5300 | 3000 |
| pZT7#2.1 | 39000 | 5000 | 2000 | 1300 | 3300 | 2500 |
| pZT7#3.0 | 4500 | 650 | 300 | 250 | 400 | 700 |
| pZT7#3.1 | 19000 | 100 | 400 | 300 | 900 | 800 |
| pZT7#3.2 | 2400 | 1000 | 300 | 250 | 400 | 350 |
| pZT7#3.3 | 500 | 800 | 400 | 250 | 300 | 800 |

*Detection limit: 250 molecules/cell.

TABLE 4

Host Strain/hTNFα accumulation after induction (%TMP)*

| VECTOR | BL21 (DE3) | MSD623 (DE3) | MSD624 (DE3) | MSD68 (DE3) | MSD101 (DE3) | MSD522 (DE3) |
|---|---|---|---|---|---|---|
| pET11a | 30 | 33 | 29 | 37 | 32 | 34 |
| pZT7#2.0 | 33 | 29 | 33 | 33 | 38 | 16 |

TABLE 4-continued

| | Host Strain/hTNFα accumulation after induction (%TMP)* | | | | | |
|---|---|---|---|---|---|---|
| VECTOR | BL21 (DE3) | MSD623 (DE3) | MSD624 (DE3) | MSD68 (DE3) | MSD101 (DE3) | MSD522 (DE3) |
| pZT7#2.1 | 33 | 36 | 46 | 47 | 44 | 47 |
| pZT7#3.0 | 31 | 28 | 39 | 36 | 34 | 36 |
| pZT7#3.1 | 37 | 27 | 38 | 37 | 38 | 36 |
| pZT7#3.2 | 39 | 32 | 48 | 47 | 43 | 42 |
| pZT7#3.3 | 44 | 38 | 48 | 47 | 45 | 39 |

*TMP = Total Microbial Protein

The data presented above show that pZT7#3.0, pZT7#3.1, pZT7#3.2 and pZT7#3.3 decrease the level of basal expression (compared to pET11a/pZT7#2.0) with all host strains tested without adversely influencing the induced productivity. pZT7#3.3 is consistently superior for all host strains tested.

EXAMPLE 3

Aliquots of E.coli strains MSD 101(DE3) pZen1798 (pET11a:TNF) and MSD 101(DE3) pZen1827 (pZT7#3.3:TNF) from glycerol stocks at −80° C. were streaked onto plates of L-agar (supplemented with ampicillin (50 μg/ml) or tetracycline (10 μg/ml) as appropriate to maintain selection) and incubated at 37° C. for 16 hours. An aliquot of each culture was then resuspended in 10 ml of sterile PBS and used to inoculate, to $OD_{550}=0.1$, 250 ml Erlenmeyer flasks containing 75 ml of:

1. L-broth (no glucose),
2. L-broth+1 g/L glucose,
3. M9 minimal medium with 2 g/L glucose, and
4. M9 minimal medium with 4 g/L glycerol.

All the growth media used above were supplemented with ampicillin (50 μg/ml) or tetracycline (10 μg/ml) as appropriate. The composition of M9 minimal medium is given in Table 5 below. The composition of L-broth medium has been described previously.

TABLE 5

| Composition of M9 minimal medium | |
|---|---|
| Component | g/L deionised water* |
| di-sodium hydrogen orthophosphate | 6.0 |
| potassium di-hydrogen orthophosphate | 3.0 |
| ammonium chloride | 1.0 |
| sodium chloride | 0.5 |
| magnesium sulphate hepta-hydrate | 1 mM |
| calcium chloride di-hydrate | 0.1 mM |
| thiamine | 4 μg/ml |
| casein hydrolysate (Oxoid L41) | 0.2 |

* Final pH adjusted to pH 7.0

The flasks were then incubated at 37° C. on a reciprocating shaker for 24 hours. The basal accumulation level of hTNFα in the un-induced cultures (summarised below in Table 6) was determined exactly as previously described.

TABLE 6

| | Growth medium/Basal hTNFα accumulation level (molecules per cell)* | | | |
|---|---|---|---|---|
| VECTOR | L-broth no glucose | L-broth 1 g/L glucose | M9 minimal 2 g/L glucose | M9 minimal 4 g/L glycerol |
| pET11a | 58000 | 24000 | 5100 | 64000 |
| pZT7#3.3 | 320 | 250 | <250 | <250 |

*Detection limit: 250 molecules/cell

This example demonstrates the wide utility of vector pZT7#3.3. Whereas pET11a shows growth medium dependant repression of expression, vector pZT7#3.3 in sharp contrast shows tight repression in both L-broth and M9 minimal growth media. This was surprising and totally unexpected. L-broth and M9 minimal growth media represent the two basic forms of microbial growth media: complex (L-broth) and minimal salts (M9).

EXAMPLE 4

The utility of vector pZT7#3.3 for the cloning and overproduction of toxic proteins is exemplified in this example using recombinant bovine pancreatic deoxyribonuclease (DNase 1). Host strains BL21 (non-expressing host background) and BL21(DE3) (expressing background) were transformed as follows. Competant cells prepared using the $CaCl_2$ method (Sambrook, Fritsch and Maniatis, 1989, "Molecular Cloning", 2nd Edition, Cold Spring Harbour Press, New York) were transformed with a range of plasmid DNA concentrations using the "heat shock" method (Sambrook, Fritsch and Maniatis, 1989, "Molecular Cloning", 2nd Edition, Cold Spring Harbour Press, New York) with pZen2006 (pAD10, the pET11 derivative expressing DNase 1 described previously), pZen 1980 (pZT7#3.3:DNase 1) and pZen1827 (pZT7#3.3:TNF) expressing hTNFα (used as a control: relatively non-toxic gene product). The transformation efficiency of each host-plasmid combination was determined as is well described in the art. The results are summarised below in Table 7.

TABLE 7

| | Host/Transformation Efficiency: transformants/μg plasmid DNA* | |
|---|---|---|
| VECTOR | BL21: non expressing background | BL21(DE3): expressing background |
| pET11a pAD10 Dnase 1 | no clones $2.2 \times 10^5$ (+/−2.2 × 10⁴) | 120 (+/−170) |

TABLE 7-continued

| | Host/Transformation Efficiency: transformants/μg plasmid DNA* | |
|---|---|---|
| VECTOR | BL21: non expressing background | BL21(DE3): expressing background |
| pZT7#3.3 Dnase 1 | $2.7 \times 10^5$ $(+/-3.6 \times 10^4)$ | $3.7 \times 10^5$ $(+/-1.4 \times 10^4)$ |
| pZT7#3.3 hTNFα | $2.5 \times 10^5$ $(+/-3.7 \times 10^4)$ | $3.5 \times 10^5$ $(+/-6.4 \times 10^4)$ |

*Data from three separate experiments (n = 3)

The above data clearly exemplifies the tight control of basal expression that is achieved using pZT7#3.3. The results show that pZT7#3.3:DNase 1 is sufficiently repressed to support transfer into a cell expressing T7 RNA polymerase (BL21(DE3)) without a deleterious effect on cell viability. Transformation efficiencies achieved are equivalent to those obtained with transformation into BL21(no T7 RNA polymerase) or to those with a relatively non-toxic gene product pZT7#3.3:hTNFα. If expression of DNase 1 had been leaky the cells would have been killed. This is in contrast to the results obtained with pET11a and pAD10. It will be clearly evident to those experienced in the art how pZT7#3.3 may be used to circumvent the problem of the deleterious effect that a heterologous protein can have on growth and productivity of recombinant cells.

The expression/accumulation of DNase 1 using BL21 (DE3) pZen1980 (pZT7#3.3:DNase 1) was determined by taking single colony of a BL21(DE3) pZen1980 transformant from the experiment described above and using this to inoculate a single Erlenmeyer flask containing 75 ml of L-broth (1 g/L glucose, 10 μg/ml tetracycline). The flask was incubated at 37° C. on a reciprocating shaker for 16 hours. This culture was then used to inoculate fresh L-broth (1 g/L glucose, 10 μg/ml tetracycline) to $OD_{550}$=0.1. The flask was then incubated at 37° C. on a reciprocating shaker until the growth reached $OD_{550}$=0.5. The culture was then induced by adding IPTG (0.5 mM final) and the incubation continued, under the conditions described, for a further 4 hours. The cells were harvested and the cell pellet stored at -20° C. The cell pellet was thawed and resuspended (10% w/v (wet weight)) in lysis buffer (10 mM Tris; pH 7.6, 2 mM calcium chloride, 100 μM benzamidine and 100 μM phenylmethyl-sulfonyl flouride (PMSF)). The cell suspension was then sonicated (20–30 second bursts followed by a period on ice) until examination of the suspension by light microscopy indicated >95% cell breakage. The cell debris was removed by centrifugation (4° C., 25000×g, 20 minutes) and DNase 1 activity in the supernatant determined by adding 100 μl of the cleared supernatant to 1 ml of Kunitz assay buffer (10 mM Tris; pH 8.0, 0.1 mM calcium chloride, 1 mM magnesium chloride and 50 μg calf thymus DNA). One "Kunitz Unit" is that amount of DNase 1 that causes an increase in the $A_{260nm}$ of 0.001/min. The results are summarised below in Table 8.

TABLE 8

| Host/Vector | Growth $OD_{550}$ at harvest | Dnase 1 Activity: Kunitz Units per litre of culture |
|---|---|---|
| BL21(DE3) pZen1980 (pZT7#3.3:DNase 1) | 4.0 | $2 \times 10^5$ |

Doherty et al (Gene, 1993, 136, pp337–340) found that on transformation of BL21(DE3) with pAD10, no viable bacterial colonies were obtained. This is essentially similar (given the standard deviation in the data) to our observations (described above in Table 7). Even with BL21(DE3) pLysS, Doherty et al found that transformants had poor viability when transferred to liquid media. In sharp contrast BL21 (DE3) transformed with pZen1980 (pZT7#3.3:DNase 1) achieves high transformation efficiencies which are equivalent to those achieved using a non-expressing host background and moreover BL21(DE3) pZen2980 transformants demonstrate high viability in liquid culture and retain the ability to express biologically active DNase 1 even after sub-culture.

EXAMPLE 5

Figure 13:
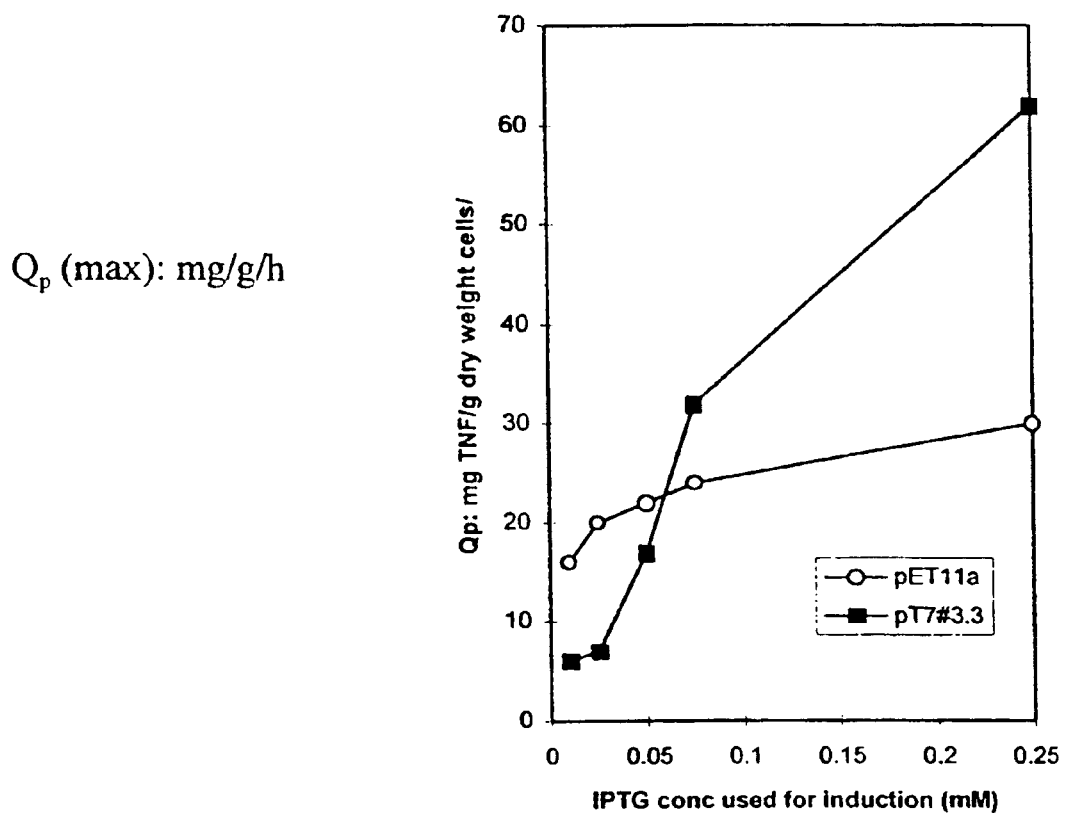
FIG. 13 shows the peak specific productivity attained at various IPTG concentrations.
Figure 14:
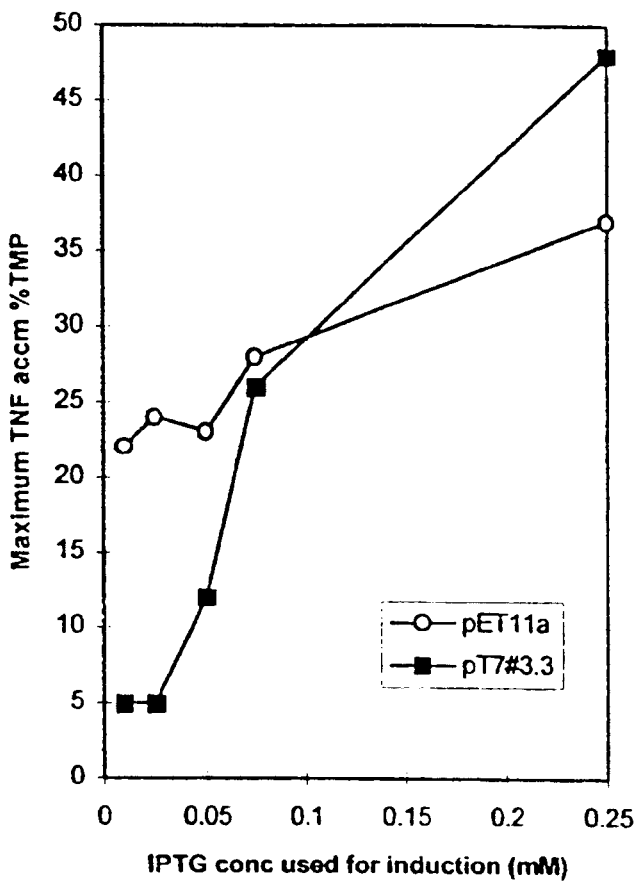
FIG. 14 shows the maximum hTNFα accumulation level attained at various IPTG concentrations.

Aliquots of E.coli strains MSD 101(DE3) pZen1798 (pET11a:TNF) and MSD 101(DE3) pZen1827 (pZT7#3.3:TNF) from glycerol stocks at -80° C. were streaked onto plates of L-agar (supplemented with ampicillin (50 μg/ml) or tetracycline (10 μg/ml) as appropriate to maintain selection) and incubated at 37° C. for 16 hours. An aliquot of each culture was used to inoculate each of two 250 ml Erlenmeyer flasks containing 75 ml of M9 minimal medium (2 g/L glucose supplemented with ampicillin (50 μg/ml) or tetracycline (10 μg/ml) as appropriate). The cultures were incubated at 37° C. for 16 hours on a reciprocal shaker and used to inoculate separately to $OD_{550}$=0.1 each of five 2 L Erlenmeyer flasks containing 600 m/l of M9 minimal medium (2 g/L glucose supplemented with ampicillin (50 μg/ml) or tetracycline (10 μg/ml) as appropriate). The composition of M9 minimal medium is given in Table 5. The flasks were incubated at 37° C. on a reciprocal shaker and the growth monitored periodically by measuring the $OD_{550}$ of the culture. When the growth reached $OD_{550}$=0.5 the cultures were induced by adding the inducer IPTG to each flask (0.25 mM, 0.075 mM, 0.05 mM, 0,025 mM and 0.01 mM (final)). The incubation was continued under the conditions described for a further 10 hours during which samples were taken for measurement of growth, accumulation of hTNFα and total microbial protein within the bacterial cells. The accumulation level of hTNFα was measured by scanning Coomassie blue stained SDS-PAGE gels of whole cell lysates of the sampled bacteria as is well known in the art. The level of total microbial protein was determined using the BCA Protein Assay Reagent (Pierce, Rockford, Ill. used in accordance with the manufacturers instructions. The accumulation level of biomass was determined by calculating the dry weight of the biomass from the $OD_{550}$ measurements as is well established in the art. The specific productivity ($Q_p$) of hTNFα (mg hTNFα produced per gram dry weight cells per hour) was calculated for each sample point during the induction period using protocols well established in the art. The $Q_{p(max)}$ (peak specific productivity) and maximum hTNFα accumulation level (% total microbial protein) attained with each IPTG concentration used for induction) are summarised in FIGS. 13 and 14 respectively (*TMP=Total microbial protein).

These results show that adding IPTG to the medium at increasing concentrations induces expression in a dose-dependant manner with pZT7#3.3. However, with pET11a expression is induced to near maximum levels even at very low concentrations of inducer. It will be evident how this surprising and unexpected property of pZT7#3.3 allows those skilled in the art to control production of heterologous proteins over a wide range of expression levels so that an optimum level of expression can be identified. This is exemplified by Examples 9 and 10.

EXAMPLE 6

E.coli strains BL21(DE3) and BL21(DE3) pLysS were transformed separately with plasmid pZen1911

(pET11a:LARd1(1275–1613) expressing LARd1 (1275–1613). *E.coli* strains MSD460(DE3) and MSD460 (DE3) pLysS were transformed separately with plasmid pZen1914 (pET11a:ZAP70(4–260)-6His) expressing ZAP70(4–260)-6His. The resultant recombinant strains were purified and maintained in glycerol stocks at −80° C. An aliquot of each culture was removed from stock and streaked separately on to L-agar plates (supplemented with ampicillin (50 μg/ml) or ampicillin (50 μg/ml) and chloramphenicol (1 μg/ml) as appropriate to maintain selection) to separate single colonies after growth for 16 hours at 37° C. A single colony of each culture was then inoculated separately into a 250 ml Erlenmeyer flasks containing 75 ml of L-broth (+1 g/L glucose and ampicillin (50 μg/ml) or ampicillin (50 μg/ml) and chloramphenicol (1 μg/ml)) as appropriate). The flasks were incubated at 37° C. on a reciprocating shaker for 16 hours. Each of these seeder cultures was then used to inoculate separately 250 ml Erlenmeyer flasks containing 75 ml L-broth (1 g/L glucose and ampicillin (50 μg/ml) or ampicillin (50 μg/ml) and chloramphenicol (1 μg/ml)) as appropriate) to $OD_{550}$=0.1. The flasks were then incubated at 20° C. on a reciprocating shaker until the growth reached $OD_{550}$=0.5. The cultures were then induced by adding IPTG (0.5 mM for LARd1 (1275–1613) and 2 mM for ZAP70(4–260)-6His) and the incubation continued, under the conditions described, for a further 24 hours. LAR d1(1275–1613) and ZAP70(4–260)-6His accumulation was measured in the seeder cultures and IPTG induced cultures described above by scanning Coomassie blue stained SDS-PAGE gels of whole cell lysates of the sampled bacteria as is well known in the art. The results are summarised below in Table 9.

TABLE 9

| HOST STRAIN | PLASMID | BASAL: (seeder culture) | INDUCED |
|---|---|---|---|
| | | Accumulation level % TMP* | |
| | | LARd1(1275–1613) | |
| BL21(DE3) | pZen1911 | 18 | 40 |
| BL21(DE3) pLysS | pZen1911 | nd[(1)] | 13 |
| | | ZAP70(4–260)-6His | |
| MSD460(DE3) | pZen1914 | 0.4 | 12 |
| MSD460(DE3) pLysS | pZen1914 | nd[(1)] | nd[(1)] |

*TMP: Total microbial protein
[(1)]not detected on Coomassie blue stained SDS-PAGE gels This example further exemplifies the poor performance of pET11a in terms of high basal expression. Reducing basal expression in the absence of inducer using pLySS reduces the-level of basal expression but adversely influences induced productivity.

EXAMPLE 7

*E.coli* strain BL21(DE3) was transformed separately with plasmids pZen1977 (pET11a:MCP-1(9–76)) and pZen1848 (pZT7#3.3:MCP-1(9–76)) expressing MCP-1(9–76). The resultant recombinant strains were purified and maintained in glycerol stocks at −80° C. An aliquot of each culture was removed from stock and streaked separately on to L-agar plates (supplemented with ampicillin (50 μg/ml) or tetracycline (10 μg/ml) as appropriate to maintain selection) to separate single colonies after growth for 16 hours at 37° C. A single colony of each culture was then inoculated into each of two 250 ml Erlenmeyer flasks containing 75 ml of L-broth (+1 g/L glucose and ampicillin (50 μg/ml) or tetracycline (10 μg/ml) as appropriate). The flasks were incubated at 37° C. on a reciprocating shaker for 16 hours. Each of these cultures was then used to inoculate three 250 ml Erlenmeyer flasks containing 75 ml L-broth (1 g/L glucose and ampicillin (50 μg/ml) or tetracycline (10 μg/ml) as appropriate) to $OD_{550}$=0.1. The flasks were then incubated at 37° C., 30° C. and 20° C. on a reciprocating shaker until the growth reached $OD_{550}$=0.5. The cultures were then induced by adding IPTG (0.25 mM final) and the incubation continued, under the conditions described, for a further 5–24 hours. MCP-1(9–76) accumulation was measured by scanning Coomassie blue stained SDS-PAGE gels of whole cell lysates of the sampled bacteria as is well known in the art. Partitioning (solubility) of MCP-1(9–76) in the cytoplasmic (soluble) and pellet (insoluble) fractions of cells was determined by subjecting sampled bacteria to sonication lysis as is well known in the art. The results are summarised below in Table 10.

TABLE 10

| VECTOR | Temperature ° C. | Induction time (h) | Accumulation MCP-1(9–76) % TMP* | Solubility % |
|---|---|---|---|---|
| pET11a: MCP-1(9–76) | 20 | 24 | 7 | 100 |
| pET11a: MCP-1(9–76) | 30 | 24 | 3 | 100 |
| pET11a: MCP-1(9–76) | 37 | 5 | 4 | 100 |
| pZT7#3.3: MCP-1(9–76) | 20 | 24 | 12 | 100 |
| pZT7#3.3: MCP-1(9–76) | 30 | 24 | 14 | 95 |
| pZT7#3.3: MCP-1(9–76) | 37 | 5 | 22 | 80 |

*TMP = Total microbial protein

The utility of vector pZT7#3.3 for high level soluble accumulation of MCP-1(9–76) is clearly evident from the data presented above.

EXAMPLE 8

*E.coli* strain MSD460(DE3) was transformed separately with plasmids pZen1914 (pET11a:ZAP70(4–260)-6His) and pZen1913 (pZT7#3.3:ZAP70(4–260)-6His) expressing ZAP70(4–260)-6His: The resultant recombinant strains were purified and maintained in glycerol stocks at −80° C. An aliquot of each culture was removed from stock and streaked separately on to L-agar plates (supplemented with ampicillin (50 μg/ml) or tetracycline (10 μg/ml) as appropriate to maintain selection) to separate single colonies after growth for 16 hours at 37° C. A single colony of each culture was then inoculated into each of two 250 ml Erlenmeyer flasks containing 75 ml of L-broth (+1 g/L glucose and ampicillin (50 μg/ml) or tetracycline (10 μg/ml) as appropriate). The flasks were incubated at 30° C. on a reciprocating shaker for 16 hours. Each of these cultures was then used to inoculate a 250 ml Erlenmeyer flask containing 75 ml L-broth (1 g/L glucose and ampicillin (50 μg/ml) or tetracycline (10 μg/ml) as appropriate) to $OD_{550}$=0.1. The flasks were then incubated at 20° C. on a reciprocating shaker until the growth reached $OD_{550}$=0.5. The cultures were then induced by adding IPTG (2 mM (final)) and the incubation continued under the conditions described, for a further 24 hours.

ZAP70(4–260)-6His accumulation after induction was measured by scanning Coomassie blue stained SDS-PAGE gels of whole cell lysates of the sampled bacteria as is well known in the art. Partitioning (solubility) of ZAP70(4–260)-6His in the cytoplasmic (soluble) and pellet (insoluble) fractions of cells was determined by subjecting sampled bacteria to sonication lysis as is well known in the art. The sonication lysis buffer included protease inhibitors (1 mM phenylmethylsulphonyl flouride (PMSF), 1 mM benzamidine and 1 mM iodoacetamide) to reduce proteolytic degradation of ZAP70(4–260)-6His during sample processing. The results are summarised below in Table 11.

TABLE 11

| VECTOR | ZAP70(4–260)-6His Accumulation % TMP* | Solubility Solubility % |
|---|---|---|
| pET11a: ZAP70(4–260)-6His | 11 | <5 |
| pZT7#3.3: ZAP70(4–260)-6His | 11 | 70 |

*TMP = Total microbial protein

The utility of vector pZT7#3.3 for the soluble accumulation of ZAP70(4–260)-6His is clearly exemplified by the data in the table above.

EXAMPLE 9

E.coli strain MSD624(DE3) was transformed separately with plasmids pZen1953 (pET11a:CPB[D253K]-6His-cmyc) and pZen1954 (pZT7#3.3:CPB[D253K]-6His-cmyc) expressing CPB[D253K]-6His-cmyc. The resultant recombinant strains were purified and maintained in glycerol stocks at −80° C. An aliquot of each culture was removed from stock and streaked separately on to L-agar plates (supplemented with ampicillin (50 µg/ml) or tetracycline (10 µg/ml) as appropriate to maintain selection) to separate single colonies after growth for 16 hours at 37° C. A single colony of each culture was then inoculated into each of two 250 ml Erlenmeyer flasks containing 75 ml of L-broth (+1 g/L glucose and ampicillin (50 µg/ml) or tetracycline (10 µg/ml) as appropriate). The flasks were incubated at 37° C. on a reciprocating shaker for 16 hours. Each of these cultures was then used to inoculate ten 2L Erlenmeyer flasks containing 600 ml L-broth (1 g/L glucose and ampicillin (50 µg/ml) or tetracycline (10 µg/ml) as appropriate) to $OD_{550}$=0.1. The flasks were then incubated at 20° C. on a reciprocating shaker until the growth reached $OD_{550}$=0.5. The cultures were then induced by adding IPTG (0.001, 0.0025, 0.005, 0.0075, 0.01, 0.025, 0.05, 0.075, 0.1 and 0.25 mM IPTG (final)) and the incubation continued, under the conditions described, for a further 48 hours. The cells were then harvested (4° C., 25000×g, 20 minutes) and subjected to osmotic shock cell fractionation (as is well known in the art) to isolate the cellular fraction containing proteins partitioned in the soluble E.coli periplasmic fraction. The accumulation of biologically active CPB[D253K]-6His-cmyc in the soluble E.coli periplasmic extract was determined by measuring the release of hippuric acid from the substrate hippuryl-L-glutamine as follows.

Cell free periplasmic extract (125 µl) was added to a test tube containing 100 µl 25 mM Tris buffer (pH 7.5), 2.5 µl 100 mM zinc chloride and 0.5 mM substrate (hippuryl-L-glutamine). This was incubated at 37° C. for 24 hours. The reaction was stopped by adding 2501 µl "Stop solution" (40% methanol (HPLC grade), 60% 50 mM phosphate buffer (Sigma P8165), 0.2% w/v trichloroacetic acid. After mixing any precipitate formed was removed by centrifugation (4° C., 16000×g, 3 minutes). The amount of hippuric acid in the cleared supernatant was then determined using HPLC as is well established in the art.

The accumulation of biologically active CPB[D253K]-6His-cmyc was determined by reference to a standard curve prepared with purified active recombinant CPB[D253K]-6His-cmyc and hippuric acid (Sigma H6375).

Figure 15:
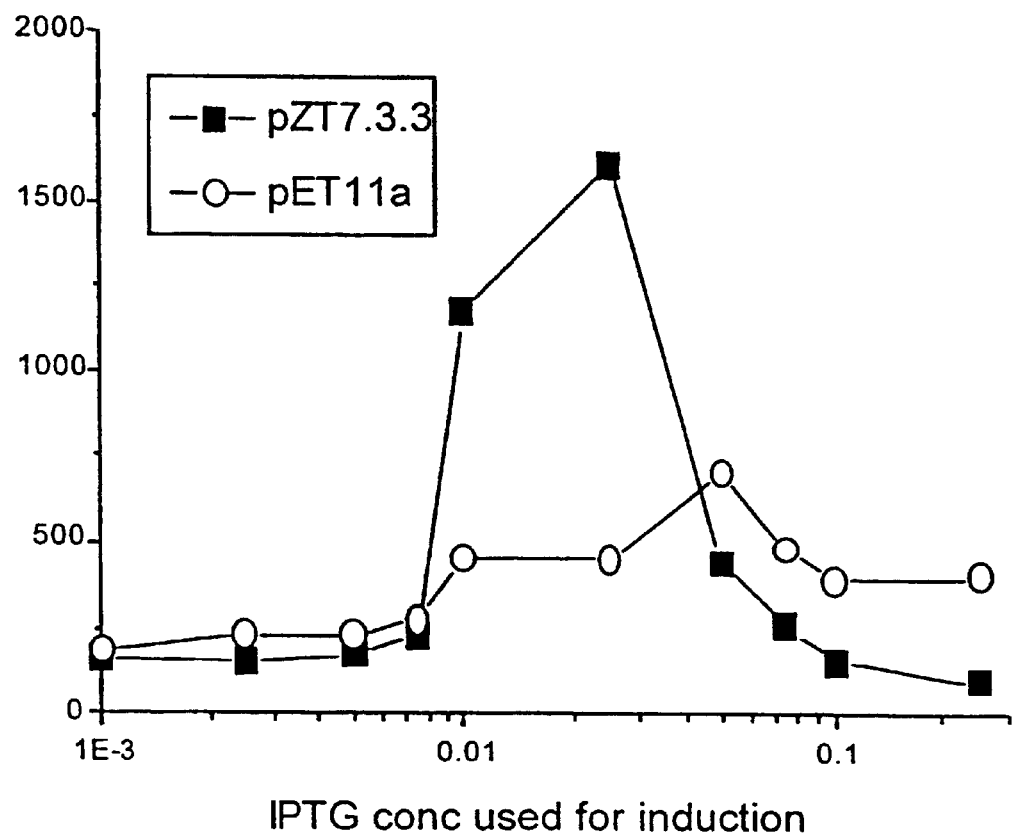
FIG. 15 shows the accumulation of biologically active CPB[D253K]-6His-cmyc (as μg active material/L of culture) attained at various IPTG concentrations.

The accumulation in the periplasm of E.coli of biologically active CPB[D253K]-6His-cmyc (as µg active material/L of culture) is presented in FIG. 15.

EXAMPLE 10

Figure 16:
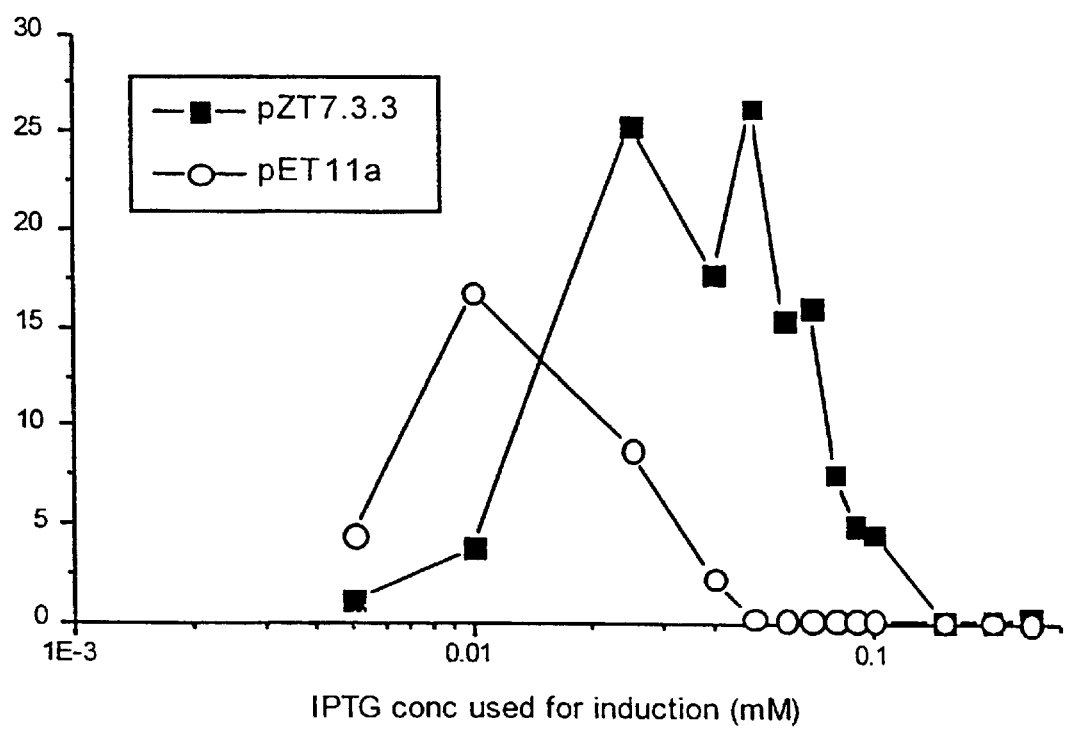
FIG. 16 shows the accumulation in the periplasm of *E.coli* of biologically active A5B7(Fab')$_2$/A5B7(Fab') (as mg active material/L of culture) attained at various IPTG concentrations.

E.coli strain MSD624(DE3) was transformed separately with plasmids pZen1999 (pET11a:A5B7(Fab')$_2$) and pZen1997 (pZT7#3.3: A5B7(Fab'$_2$) expressing A5B7(Fab')$_2$. The resultant recombinant strains were purified and maintained in glycerol stocks at −80° C. An aliquot of each culture was removed from stock and streaked separately on to L-agar plates (supplemented with ampicillin (50 µg/ml) or tetracycline (10 µg/ml) as appropriate to maintain selection) to separate single colonies after growth for 16 hours at 37° C. A single colony of each culture was then inoculated into each of two 250 ml Erlenmeyer flasks containing 75 ml of L-broth (+1 g/L glucose and ampicillin (50 µg/ml) or tetracycline (10 µg/ml) as appropriate). The flasks were incubated at 37° C. on a reciprocating shaker for 16 hours. Each of these cultures was then used to inoculate thirteen 2 L Erlenmeyer flasks containing 600 ml L-broth (1 g/L glucose and ampicillin (50 µg/ml) or tetracycline (10 µg/ml) as appropriate) to $OD_{550}$=0.1. The flasks were then incubated at 20° C. on a reciprocating shaker until the growth reached $OD_{550}$=0.5. The cultures were then induced by adding IPTG (0.005, 0.01, 0.025, 0.04, 0.05, 0.06, 0.07, 0.08,.0.09, 0.1, 0.15, 0.2 and 0.25 mM IPTG (final)) and the incubation continued, under the conditions described, for a further 48 hours. The cells were then harvested (4° C., 25000×g, 20 minutes) and subjected to osmotic shock cell fractionation (as is well known in the art) to isolate the cellular fraction containing proteins partitioned in the soluble E.coli periplasmic fraction. The accumulation of biologically active A5B7(Fab')$_2$/A5B7(Fab') in the soluble E.coli periplasmic extract was estimated by determining the binding of A5B7 (Fab')$_2$/A5B7(Fab') to human tumour carcinoembryonic antigen (CEA) in an ELISA assay. The accumulation in the periplasm of E.coli of biologically active A5B7(Fab')$_2$/A5B7(Fab') (as mg active material/L of culture) is presented in FIG. 16.

With both proteins (described in Examples 9 and 10 above), pZT7#3.3 accumulates higher levels of active product in the periplasm of E.coli than pET11a. The data presented in FIGS. 15–16 clearly demonstrates how the modulation characteristics of pZT7#3.3 can be exploited to optimise recombinant protein yields. These examples exemplify the use of pZT7#3.3 vector for secretion. However, it will be readily apparent to those skilled in the art how the basal level of expression/modulation of expression characteristics of pZT7#3.3 also facilitates the expression and accumulation of heterologous membrane proteins.

TABLE 12

| | |
|---|---|
| PCR primer #1 (lac I 5'-3') | |
| GATGCTATAATGCATGACACCATCGAATGGCGCAA | SEQ ID NO:1 |
| PCR primer #2 (lacI 3'-5') | |
| CAGTATGCACAGTATGCATTTACATTAATTGCGTTGCGCTC | SEQ ID NO:2 |
| 5'-3' oligomer #3 | |
| AATTCcagaCATATGGTACCAGTACTctatACTAGTtgaaGGATCCatgcCTCGAGaacgCTGCAGagctAAGCTTgacaAGATCTaa | SEQ ID NO:3 |
| 3'-5' oligomer #4 | |
| gatcttAGATCTtgtcAAGCTTagctCTGCAGcgttCTCGAGgcatGGATCCttcaACTAGTatagAGTACTGGTACCATATGtctgG | SEQ ID NO:4 |
| 5'-3' oligomer #5 | |
| agcttAACAAAGCCCGAAAGGAAGCTGAGTTGGCTGCTGCCACCGCTGAGCAATAACTAGCATAACCCCTTGGGGCCTCTAAACGGGTCTTGAGGGGTTTTTTGa | SEQ ID NO:5 |
| 3'-5' oligomer #6 | |
| gatctCAAAAAACCCCTCAAGACCCGTTTAGAGGCCCCAAGGGGTTATGCTAGTTATTGCTCAGCGGTGGCAGCAGCCAACTCAGCTTCCTTTCGGGCTTTGTTa | SEQ ID NO:6 |
| 5'-3' oligomer #7 | |
| tcgagGCATTGTCCTCTTAGTTAAATGGATATAACGAGCCCCTCCTAAGGGCTAATTGCAGGTTCGATTCCTGCAGGGGACTCCActgca | SEQ ID NO:7 |
| 3'-5' oligomer #8 | |
| gTGGAGTCCCCTGCAGGAATCGAACCTGCAATTAGCCCTTAGGAGGGGCTCGTTATATCCATTTAACTAAGAGGACAATGCc | SEQ ID NO:8 |
| 5'-3' oligomer #9 | |
| cctATTATATTACTAATTAATTGGGGACCCTAGAGGTCCCCTTTTTTATTTTAAAAccatggaaccaaccg | SEQ ID NO:9 |
| 3'-5' oligomer #10 | |
| aattcggttggttccatggTTTTAAAATAAAAAAGGGGACCTCTAGGGTCCCCAATTAATTAGTAATATAATagg | SEQ ID NO:10 |
| 5'-3' oligomer #11 | |
| aattcCGAAATTAATACGACTCACTATAGGGGAATTGTGAGCGGATAACAATTCCCCTCTAGAAATAATTTTGTTTAACTTTAAGAAGGAGATATAca | SEQ ID NO:11 |
| 3'-5' oligomer #12 | |
| tatgTATATCTCCTTCTTAAAGTTAAACAAAATTATTTCTAGAGGGGAATTGTTATCCGCTCACAATTCCCCTATAGTGAGTCGTATTAATTTCGg | SEQ ID NO:12 |
| 5'-3' oligomer #13 | |
| aattcCGAAATTAATACGACTCACTATAGGGGAATTGTGAGCGCTCACAATTCCCCTCTAGAAATAATTTTGTTTAACTTTAAGAAGGAGATATAca | SEQ ID NO:13 |
| 3'-5' oligomer #14 | |
| tatgTATATCTCCTTCTTAAAGTTAAACAAAATTATTTCTAGAGGGGAATTGTGAGCGCTCACAATTCCCCTATAGTGAGTCGTATTAATTTCGg | SEQ ID NO:14 |
| 5'-3' oligomer #15 | |
| catggACTGGTTAACAACCAACCGGAATTGTGAGCGGATAACAATTCCTCCAAGAACAACCATCCTAGCAACACGGCGGTCCCCg | SEQ ID NO:15 |
| 3'-5' oligomer #16 | |
| aattcGGGGACCGCCGTGTTGCTAGGATGGTTGTTCTTGGAGGAATTGTTATCCGCTCACAATTCCGGTTGGTTGTTAACACGTc | SEQ ID NO:16 |
| 5'-3' oligomer #17 | |
| catggACGTGTTAACAACCAACCGGAATTGTGAGCGCTCACAATTCCATCCAAGAACAACCATCCTAGCAACACGGCGGTCCCCg | SEQ ID NO:17 |
| 3'-5' oligomer #18 | |
| aattcGGGGACCGCCGTGTTGCTAGGATGGTTGTTCTTGGATGGAATTGTGAGCGCTCACAATTCCGGTTGGTTGTTAACACGTC | SEQ ID NO:18 |

TABLE 13 hTNFα sequence SEQ ID NOS: 19–20

```
NdeI
CATATGGTACGTAGCTCCTCTCGCACTCCGTCCGATAAGCCGGTTGCTCAT
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
GTATACCATGCATCGAGGAGAGCGTGAGGCAGGCTATTCGGCCAACGAGTA

GTAGTTGCTAACCCTCAGGCAGAAGGTCAGCTGCAGTGGCTGAACCGTC
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CATCAACGATTGGGAGTCCGTCTTCCAGTCGACGTCACCGACTTGGCAG

GCGCTAACGCCCTGCTGGCAAACGGCGTTGAGCTCCGTGATAACCAGCTCG
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CGCGATTGCGGGACGACCGTTTGCCGCAACTCGAGGCACTATTGGTCGAGC

TGGTACCTTCTGAAGGTCTGTACCTGATCTATTCTCAAGTACTGTTCAA
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
ACCATGGAAGACTTCCAGACATGGACTAGATAAGAGTTCATGACAAGTT

GGGTCAGGGCTGCCCGTCGACTCATGTTCTGCTGACTCACACCATCAGCCG
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CCCAGTCCCGACGGGCAGCTGAGTACAAGACGACTGAGTGTGGTAGTCGGC

TATTGCTGTATCTTACCAGACCAAAGTTAACCTGCTGAGCGCTATCAAG
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
ATAACGACATAGAATGGTCTGGTTTCAATTGGACGACTCGCGATAGTTC

TCTCCGTGCCAGCGTGAAACTCCCGAGGGTGCAGAAGCGAAACCATGGTAT
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
AGAGGCACGGTCGCACTTTGAGGGCTCCCACGTCTTCGCTTTGGTACCATA

GAACCGATCTACCTGGGTGGCGTATTTCAACTGGAGAAAGGTGACCGTC
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CTTGGCTAGATGGACCCACCGCATAAAGTTGACCTCTTTCCACTGGCAG

TGTCCGCAGAAATCAACCGTCCTGACTATCTAGATTTCGCTGAATCTGGCC
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
ACAGGCGTCTTTAGTTGGCAGGACTGATAGATCTAAAGCGACTTAGACCGG

BamHI
AGGTGTACTTCGGTATTATCGCACTGTAATAATAAGGATCC
├┼┼┼┼┼┼┼┼┼┤┼┼┼┼┼┼┼┼┼┤┼┼┼┼┼┼┼┼┼┤┼┼┼┼┼┼┼┼┼┤▶
TCCACATGAAGCCATAATAGCGTGACATTATTATTCCTAGG
```

TABLE 14

ZAP70 (4-260) 6HIS sequence SEQ ID NOS: 21–22

```
NdeI
CATATGCCCGCGGCGCACCTGCCCTTCTTCTACGGCAGCATCTCGCGTGCCGAGGCCGAGGAGCACCTGAAGCTGGCGGG
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
GTATACGGGCGCCGCGTGGACGGGAAGAAGATGCCGTCGTAGAGCGCACGGCTCCGGCTCCTCGTGGACTTCGACCGCCC

CATGGCGGACGGGCTCTTCCTGCTGCGCCAGTGCCTGCGCTCGCTGGGCGGCTATGTGCTGTCGCTCGTGCACGATGTGC
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
GTACCGCCTGCCCGAGAAGGACGACGCGGTCACGGACGCGAGCGACCCGCCGATACACGACAGCGAGCACGTGCTACACG

GCTTCCACCACTTTCCCATCGAGCGCCAGCTCAACGGCACCTACGCCATTGCCGGCGGCAAAGCGCACTGTGGACCGGCA
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CGAAGGTGGTGAAAGGGTAGCTCGCGGTCGAGTTGCCGTGGATGCGGTAACGGCCGCCGTTTCGCGTGACACCTGGCCGT

GAGCTCTGCGAGTTCTACTCGCGCGACCCCGACGGGCTGCCCTGCAACCTGCGCAAGCCGTGCAACCGGCCGTCGGGCCT
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
CTCGAGACGCTCAAGATGAGCGCGCTGGGGCTGCCCGACGGGACGTTGGACGCGTTCGGCACGTTGGCCGGCAGCCCGGA

CGAGCCGCAGCCGGGGGTCTTCGACTGCCTGCGAGACGCCATGGTGCGTGACTACGTGCGCCAGACGTGAAGCTGGAGG
├┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤┼┼┼┼┼┼┼┼┼┤
GCTCGGCGTCGGCCCCCAGAAGCTGACGGACGCTCTGCGGTACCACGACTGATGCACGCGGTGTGCACCTTCGACCTCC
```

TABLE 14-continued

ZAP70 (4-260) 6HIS sequence SEQ ID NOS: 21–22

```
GCGAGGCCCTGGAGCAGGCCATCATCAGCCAGGCCCCGCAGGTGGAGAAGCTCATTGCTACGACGGCCCACGAGCGGATG
|+++|++++|++++|++++|++++|++++|++++|++++|++++|++++|++++|++++|++++|++++|++++|++++| 48
CGCTCCGGGACCTCGTCCGGTAGTAGTCGGTCCGGGGCGTCCACCTCTTCGAGTAACGATGCTGCCGGGTGCTCGCCTAC

CCCTGGTACCACAGCAGCCTGACGCGTGAGGAGGCCGAGCGCAAACTTTACTCTGGGGCGCAGACCGACGGCAAGTTCCT
|+++|++++|++++|++++|++++|++++|++++|++++|++++|++++|++++|++++|++++|++++|++++|++++| 56
GGGACCATGGTGTCGTCGGACTGCGCACTCCTCCGGCTCGCGTTTGAAATGAGACCCCGCGTCTGGCTGCCGTTCAAGGA

GCTGAGGCCGCGGAAGGAGCAGGGCACATACGCCCTGTCCCTCATCTATGGGAAGACGGTGTACCACTACCTCATCAGCC
|+++|++++|++++|++++|++++|++++|++++|++++|++++|++++|++++|++++|++++|++++|++++|++++| 64
CGACTCCGGCGCCTTCCTCGTCCCGTGTATGCGGGACAGGGAGTAGATACCCTTCTGCCACATGGTGATGGAGTAGTCGG

AAGACAAGGCGGGCAAGTACTGCATTCCCGAGGGCACCAAGTTTGACACGCTCTGGCAGCTGGTGGAGTATCTGAAGCTG
|+++|++++|++++|++++|++++|++++|++++|++++|++++|++++|++++|++++|++++|++++|++++|++++| 72
TTCTGTTCCGCCCGTTCATGACGTAAGGGCTCCCGTGGTTCAAACTGTGCGAGACCGTCGACCACCTCATAGACTTCGAC

AAGGCGGACGGGCTCATCTACTGCCTGAAGGAGGCCTGCCCCAACAGCAGTGCCAGCCATCACCATCACCATCACTAATA
|+++|++++|++++|++++|++++|++++|++++|++++|++++|++++|++++|++++|++++|++++|++++|++++| 80
TTCCGCCTGCCCGAGTAGATGACGGACTTCCTCCGGACGGGGTTGTCGTCACGGTCGGTAGTGGTAGTGGTAGTGATTAT

BgI II
  :
AAGATCT
|+++|+▶ 807
TTCTAGA
```

TABLE 15

LARd1 (aa1275–1623) sequence SEQ ID NOS: 25–26

```
  NdeI
  :
CATATGGTACCAACCCACTCTCCGTCCTCTAAGGATGAGCAGTCGATCGGACTGAAGGACTCCTTGCTGGCCCACTCCTCTGACCCTGTG
|+++|++++|++++|++++|++++|++++|++++|++++|++++|++++|++++|++++|++++|++++|++++|++++|++++|++++| 90
GTATACCATGGTTGGGTGAGAGGCAGGAGATTCCTACTCGTCAGCTAGCCTGACTTCCTGAGGAACGACCGGGTGAGGAGACTGGGACAC

GAGATGCGGAGGCTCAACTACCAGACCCCAGGTATGCGAGACCACCCACCCATCCCCATCACCGACCTGGCGGACAACATCGAGCGCCTC
|+++|++++|++++|++++|++++|++++|++++|++++|++++|++++|++++|++++|++++|++++|++++|++++|++++|++++| 18
CTCTACGCCTCCGAGTTGATGGTCTGGGGTCCATACGCTCTGGTGGGTGGGTAGGGGTAGTGGCTGGACCGCCTGTTGTAGCTCGCGGAG

AAAGCCAACGATGGCCTCAAGTTCTCCCAGGAGTATGAGTCCATCGACCCTGGACAGCAGTTCACGTGGGAGAATTCAAACCTGGAGGTG
|+++|++++|++++|++++|++++|++++|++++|++++|++++|++++|++++|++++|++++|++++|++++|++++|++++|++++| 27
TTTCGGTTGCTACCGGAGTTCAAGAGGGTCCTCATACTCAGGTAGCTGGGACCTGTCGTCAAGTGCACCCTCTTAAGTTTGGACCTCCAC

AACAAGCCCAAGAACCGCTATGCGAATGTCATCGCCTACGACCACTCTCGAGTCATCCTTACCTCTATCGATGGCGTCCCCGGGAGTGAC
|+++|++++|++++|++++|++++|++++|++++|++++|++++|++++|++++|++++|++++|++++|++++|++++|++++|++++| 36
TTGTTCGGGTTCTTGGCGATACGCTTACAGTAGCGGATGCTGGTGAGAGCTCAGTAGGAATGGAGATAGCTACCGCAGGGGCCCTCACTG

TACATCAATGCCAACTACATCGATGGCTACCGCAAGCAGAATGCCTACATCGCCACGCAGGGCCCCCTGCCCGAGACCATGGGCGATTTC
|+++|++++|++++|++++|++++|++++|++++|++++|++++|++++|++++|++++|++++|++++|++++|++++|++++|++++| 45
ATGTAGTTACGGTTGATGTAGCTACCGATGGCGTTCGTCTTACGGATGTAGCGGTGCGTCCCGGGGACGGGCTCTGGTACCCGCTAAAG

TGGAGAATGGTGTGGGAACAGCGCACGGCCACTGTGGTCATGATGACACGGCTGGAGGAGAAGTCCCGGGTAAAATGTGATCAGTACTGG
|+++|++++|++++|++++|++++|++++|++++|++++|++++|++++|++++|++++|++++|++++|++++|++++|++++|++++| 54
ACCTCTTACCACACCCTTGTCGCGTGCCGGTGACACCAGTACTACTGTGCCGACCTCCTCTTCAGGGCCCATTTTACACTAGTCATGACC
```

TABLE 15-continued

LARd1 (aa1275–1623) sequence SEQ ID NOS: 25–26

```
CCAGCCCGTGGCACCGAGACCTGTGGCCTTATTCAGGTGACCCTGTTGGACACAGTGGAGCTGGCCACATACACTGTGCGCACCTTCGCA
++++++++|++++++++|++++++++|++++++++|++++++++|++++++++|++++++++|++++++++|++++++++|  18
GGTCGGGCACCGTGGCTCTGGACACCGGAATAAGTCCACTGGGACAACCTGTGTCACCTCGACCGGTGTATGTGACACGCGTGGAAGCGT

CTCCACAAGAGTGGCTCCAGTGAGAAGCGTGAGCTGCGTCAGTTTCAGTTCATGGCCTGGCCAGACCATGGAGTTCCTGAGTACCCAACT
++++++++|++++++++|++++++++|++++++++|++++++++|++++++++|++++++++|++++++++|++++++++|  72
GAGGTGTTCTCACCGAGGTCACTCTTCGCACTCGACGCAGTCAAAGTCAAGTACCGGACCGGTCTGGTACCTCAAGGACTCATGGGTTGA

CCCATCCTGGCCTTCCTACGACGGGTCAAGGCCTGCAACCCCCTAGACGCAGGGCCCATGGTGGTGCACTGCAGCGCGGGCGTGGGCCGC
++++++++|++++++++|++++++++|++++++++|++++++++|++++++++|++++++++|++++++++|++++++++|  81
GGGTAGGACCGGAAGGATGCTGCCCAGTTCCGGACGTTGGGGGATCTGCGTCCCGGGTACCACCACGTGACGTCGCGCCCGCACCCGGCG

ACCGGCTGCTTCATCGTGATTGATGCCATGTTGGAGCGGATGAAGCACGAGAAGACGGTGGACATCTATGGCCACGTGACCTGCATGCGA
++++++++|++++++++|++++++++|++++++++|++++++++|++++++++|++++++++|++++++++|++++++++|  90
TGGCCGACGAAGTAGCACTAACTACGGTACAACCTCGCCTACTTCGTGCTCTTCTGCCACCTGTAGATACCGGTGCACTGGACGTACGCT

TCACAGAGGAACTACATGGTGCAGACGGAGGACCAGTACGTGTTCATCCATGAGGCGCTGCTGGAGGCTGCCACGTGCGGCCACACAGAG
++++++++|++++++++|++++++++|++++++++|++++++++|++++++++|++++++++|++++++++|++++++++|  99
AGTGTCTCCTTGATGTACCACGTCTGCCTCCTGGTCATGCACAAGTAGGTACTCCGCGACGACCTCCGACGGTGCACGCCGGTGTGTCTC

BgI II
                                  ⋮
GTGCCTGCCCGCAACCTGTATGCCCACTAATGAAGATCT
++++++++|++++++++|++++++++|++++++++► 1029
CACGGACGGGCGTTGGACATACGGGTGATTACTTCTAGA
```

TABLE 16

Bovine pancreatic DNase 1 sequence SEQ ID NOS: 25–26

```
NdeI
⋮
CATATGCTTAAGATCGCTGCTTTCAACATACGTACCTTCGGTGAATCTA
++++++++|++++++++|++++++++|++++++++|++++++
GTATACGAATTCTAGCGACGAAAGTTGTATGCATGGAAGCCACTTAGAT

AAATGTCTAACGCTACGCTAGCATCTTACATCGTACGCATCGTACGCCGTT
++++++++|++++++++|++++++++|++++++++|++++++++|+
TTTACAGATTGCGATGCGATCGTAGAATGTAGCATGCGTAGCATGCGGCAA

ACGATATCGTTCTGATCCAGGAAGTTCGCGACTCTCACCTGGTTGCAGT
++++++++|++++++++|++++++++|++++++++|++++++++|
TGCTATAGCAAGACTAGGTCCTTCAAGCGCTGAGAGTGGACCAACGTCA

TGGTAAACTTCTAGACTACCTGAACCAGGACGACCCGAACACCTACCACTA
++++++++|++++++++|++++++++|++++++++|++++++++|+
ACCATTTGAAGATCTGATGGACTTGGTCCTGCTGGGCTTGTGGATGGTGAT

CGTTGTTTCTGAACCCCTCGGGCGTAACTCTTACAAAGAACGGTACCTG
++++++++|++++++++|++++++++|++++++++|++++++++|
GCAACAAAGACTTGGGGAGCCCGCATTGAGAATGTTTCTTGCCATGGAC

TTCCTGTTCCGTCCGAACAAAGTTTCAGTACTGGATACCTACCAGTACGAC
++++++++|++++++++|++++++++|++++++++|++++++++|+
AAGGACAAGGCAGGCTTGTTTCAAAGTCATGACCTATGGATGGTCATGCTG

GACGGATGCGAATCTTGCGGTAACGACTCTTTCTCCCGGGAACCGGCTG
++++++++|++++++++|++++++++|++++++++|++++++++|
CTGCCTACGCTTAGAACGCCATTGCTGAGAAAGAGGGCCCTTGGCCGAC

TTGTTAAATTCTCGAGCCACTCTACCAAGGTTAAAGAGTTCGCTATCGTTG
++++++++|++++++++|++++++++|++++++++|++++++++|+
AACAATTTAAGAGCTCGGTGAGATGGTTCCAATTTCTCAAGCGATAGCAAC

CTCTGCACAGCGCGCCGTCTGACGCTGTTGCTGAAATCAACTCTCTGTA
++++++++|++++++++|++++++++|++++++++|++++++++|
GAGACGTGTCGCGCGGCAGACTGCGACAACGACTTTAGTTGAGAGACAT

CGACGTTTACCTGGACGTTCAGCAGAAATGGCACCTGAACGACGTCATGCT
++++++++|++++++++|++++++++|++++++++|++++++++|+
GCTGCAAATGGACCTGCAAGTCGTCTTTACCGTGGACTTGCTGCAGTACGA

GATGGGTGACTTCAACGCTGACTGCTCTTATGTAACCTCTTCTCAGTGG
++++++++|++++++++|++++++++|++++++++|++++++++
CTACCCACTGAAGTTGCGACTGACGAGAATACATTGGAGAAGAGTCACC

TCATCGATTCGTCTGCGCACCTCGTCGACCTTCCAGTGGCTGATCCCGGAC
++++++++|++++++++|++++++++|++++++++|++++++++|+
AGTAGCTAAGCAGACGCGTGGAGCAGCTGGAAGGTCACCGACTAGGGCCTG

TCCGCTGACACCACCGCTACTAGTACCAACTGCGCTTACGACCGTATCG
++++++++|++++++++|++++++++|++++++++|++++++++
AGGCGACTGTGGTGGCGATGATCATGGTTGACGCGAATGCTGGCATAGC

TTGTTGCTGGATCCCTGCTGCAGTCTTCTGTTGTACCGGGTAGCGCGGCC
++++++++|++++++++|++++++++|++++++++|++++++++|+
AACAACGACCTAGGGACGACGTCAGAAGACAACATGGCCCATCGCGCCGGG

CGTTCGACTTCCAGGCTGCGTATGGTCTTTCGAACGAAATGGCGCTGGCC
++++++++|++++++++|++++++++|++++++++|++++++++|
GCAAGCTGAAGGTCCGACGCATACCAGAAAGCTTGCTTTACCGCGACCGG

BgI II
                                              ⋮
ATCTCTGATCACTACCCGGTTGAGGTTACCCTGACCTAATAGAGATCT
++++++++|++++++++|++++++++|++++++++|++++++++►798
TAGAGACTAGTGATGGGCCAACTCCAATGGGACTGGATTATCTCTAGA
```

TABLE 17 human carboxypeptidase B (mutant D253>K) 6His cmyc sequence SEQ ID NOS: 27–28

```
ATGAAATACCTATTGCCTACGGCAGCCGCTGGATTGTTATTACTCGCTGCCCAACCAGCCATGGCGGCAACTGGTCACTCTTACGAGAAG
++++++++++++++++++++++++++++++++++++++++++++++++++++++++++++++++++++++++++++++++++++++++++  90
TACTTTATGGATAACGGATGCCGTCGGCGACCTAACAATAATGAGCGACGGGTTGGTCGGTACCGCCGTTGACCAGTGAGAATGCTCTTC

TACAACAAGTGGGAAACGATAGAGGCTTGGACTCAACAAGTCGCCACTGAGAATCCAGCCCTCATCTCTCGCAGTGTTATCGGAACCACA
++++++++++++++++++++++++++++++++++++++++++++++++++++++++++++++++++++++++++++++++++++++++++  18
ATGTTGTTCACCCTTTGCTATCTCCGAACCTGAGTTGTTCAGCGGTGACTCTTAGGTCGGGAGTAGAGAGCGTCACAATAGCCTTGGTGT

TTTGAGGGACGCGCTATTTACCTCCTGAAGGTTGGCAAAGCTGGACAAAATAAGCCTGCCATTTTCATGGACTGTGGTTTCCATGCCAGA
++++++++++++++++++++++++++++++++++++++++++++++++++++++++++++++++++++++++++++++++++++++++++  27
AAACTCCCTGCGCGATAAATGGAGGACTTCCAACCGTTTCGACCTGTTTTATTCGGACGGTAAAAGTACCTGACACCAAAGGTACGGTCT

GAGTGGATTTCTCCTGCATTCTGCCAGTGGTTTGTAAGAGAGGCTGTTCGTACCTATGGACGTGAGATCCAAGTGACAGAGCTTCTCGAC
++++++++++++++++++++++++++++++++++++++++++++++++++++++++++++++++++++++++++++++++++++++++++  36
CTCACCTAAAGAGGACGTAAGACGGTCACCAAACATTCTCTCCGACAAGCATGGATACCTGCACTCTAGGTTCACTGTCTCGAAGAGCTG

AAGTTAGACTTTTATGTCCTGCCTGTGCTCAATATTGATGGCTACATCTACACCTGGACCAAGAGCCGATTTTGGAGAAAGACTCGCTCC
++++++++++++++++++++++++++++++++++++++++++++++++++++++++++++++++++++++++++++++++++++++++++  45
TTCAATCTGAAAATACAGGACGGACACGAGTTATAACTACCGATGTAGATGTGGACCTGGTTCTCGGCTAAAACCTCTTTCTGAGCGAGG

ACCCATACTGGATCTAGCTGCATTGGCACAGACCCCAACAGAAATTTTGATGCTGGTTGGTGTGAAATTGGAGCCTCTCGAAACCCCTGT
++++++++++++++++++++++++++++++++++++++++++++++++++++++++++++++++++++++++++++++++++++++++++  54
TGGGTATGACCTAGATCGACGTAACCGTGTCTGGGGTTGTCTTTAAAACTACGACCAACCACACTTTAACCTCGGAGAGCTTTGGGGACA

GATGAAACTTCATGTGGACCTGCCGCAGAGTCTGAAAAGGAGACCAAGGCCCTGGCTGATTTCATCCGCAACAAACTCTCTTCCATCAAG
++++++++++++++++++++++++++++++++++++++++++++++++++++++++++++++++++++++++++++++++++++++++++  63
CTACTTTGAATGACACCTGGACGGCGTCTCAGACTTTTCCTCTGGTTCCGGGACCGACTAAAGTAGGCGTTGTTTGAGAGAAGGTAGTTC

GCATATCTGACAATCCACTCGTACTCCCAAATGATGATCTACCCTTACTCATATGCTTACAAACTCGGTGAGAACAATGCTGAGTTGAAT
++++++++++++++++++++++++++++++++++++++++++++++++++++++++++++++++++++++++++++++++++++++++++  72
CGTATAGACTGTTAGGTGAGCATGAGGGTTTACTACTAGATGGGAATGAGTATACGAATGTTTGAGCCACTCTTGTTACGACTCAACTTA

GCCCTGGCTAAAGCTACTGTGAAAGAACTTGCCTCACTGCACGGCACCAAGTACACATATGGCCCGGGAGCTACAACAATCTATCCTGCT
++++++++++++++++++++++++++++++++++++++++++++++++++++++++++++++++++++++++++++++++++++++++++  81
CGGGACCGATTTCGATGACACTTTCTTGAACGGAGTGACGTGCCGTGGTTCATGTGTATACCGGGCCCTCGATGTTGTTAGATAGGACGA

GCTGGGGGCTCTAAAGACTGGGCTTATGACCAAGGAATCAGATATTCCTTCACCTTTGAACTTCGAGATACAGGCAGATATGGCTTTCTC
++++++++++++++++++++++++++++++++++++++++++++++++++++++++++++++++++++++++++++++++++++++++++  90
CGACCCCCGAGATTTCTGACCCGAATACTGGTTCCTTAGTCTATAAGGAAGTGGAAACTTGAAGCTCTATGTCCGTCTATACCGAAAGAG

CTTCCAGAATCCCAGATCCGGGCTACCTGCGAGGAGACCTTCCTGGCAATCAAGTATGTTGCCAGCTACGTCCTGGAACACCTGTACCAC
++++++++++++++++++++++++++++++++++++++++++++++++++++++++++++++++++++++++++++++++++++++++++  99
GAAGGTCTTAGGGTCTAGGCCCGATGGACGCTCCTCTGGAAGGACCGTTAGTTCATACAACGGTCGATGCAGGACCTTGTGGACATGGTG

CACCATCACCACCATGAGTTCGAGGAGCAGAAGCTGATCTCTGAGGAGGACCTGAACTAATAA
+++++++++++++++++++++++++++++++++++++++++++++++++++++++++++►  1053
GTGGTAGTGGTGGTACTCAAGCTCCTCGTCTTCGACTAGAGACTCCTCCTGGACTTGATTATT
```

TABLE 19

Human monocyte chemotactic protein MCP-1 (9–76) sequence SEQ ID NOS: 29–30

```
ATGGTTACCTGCTGTTATAACTTCACCAACCGTAAAATCTCAGTGCAGAGGCTCGCGAGCTATAGAAGAATCACCAGCAGCAAGTGTCCC
++++++++++++++++++++++++++++++++++++++++++++++++++++++++++++++++++++++++++++++++++++++++++  90
TACCAATGGACGACAATATTGAAGTGGTTGGCATTTTAGAGTCACGTCTCCGAGCGCTCGATATCTTCTTAGTGGTCGTCGTTCACAGGG

AAAGAAGCTGTGATCTTCAAGACCATTGTGGCCAAGGAGATCTGTGCTGACCCCAAGCAGAAGTGGGTTCAGGATTCCATGGACCACCTG
++++++++++++++++++++++++++++++++++++++++++++++++++++++++++++++++++++++++++++++++++++++++++  18
TTTCTTCGACACTAGAAGTTCTGGTAACACCGGTTCCTCTAGACACGACTGGGGTTCGTCTTCACCCAAGTCCTAAGGTACCTGGTGGAC

GACAAGCAAACCCAAACTCCGAAGACTTGATGA
++++++++++++++++++++++++++++++►  213
CTGTTCGTTTGGGTTTGAGGCTTCTGAACTACT
```

TABLE 20

A5B7 F(ab')₂ sequences SEQ ID NOS: 31–32

```
CATATGAAATACCTATTGCCTACGGCAGCCGCTGGATTGTTATTACTCGCTGCCCAACCAGCGATGG
GTATACTTTATGGATAACGGATGCCGTCGGCGACCTAACAATAATGAGCGACGGGTTGGTCGCTACC
CCCAGGTGCAGCTGCAGGAATCTGGTGGTGGCTTAGTTCAACCTGGTGGTTCCCTGAGACTCT
GGGTCCACGTCGACGTCCTTAGACCACCACCGAATCAAGTTGGACCACCAAGGGACTCTGAGA
CCTGTGCAACTTCTGGGTTCACCTTCACTGATTACTACATGAACTGGGTCCGCCAGCCTCCAGGAAA
GGACACGTTGAAGACCCAAGTGGAAGTGACTAATGATGTACTTGACCCAGGCGGTCGGAGGTCCTTT
GGCACTTGAGTGGTTGGGTTTTATTGGAAACAAAGCTAATGGTTACACAACAGAGTACAGTGC
CCGTGAACTCACCAACCCAAAATAACCTTTGTTTCGATTACCAATGTGTTGTCTCATGTCACG
ATCTGTGAAGGGTCGGTTCACCATCTCCAGAGATAAATCCCAAAGCATCCTCTATCTTCAAATGAAC
TAGACACTTCCCAGCCAAGTGGTAGAGGTCTCTATTTAGGGTTTCGTAGGAGATAGAAGTTTACTTC
ACCCTGAGAGCTGAGGACAGTGCCACTTATTACTGTACAAGAGATAGGGGGCTACGGTTCTAC
TGGGACTCTCGACTCCTGTCACGGTGAATAATGACATGTTCTCTATCCCCCGATGCCAAGATG
TTTGACTACTGGGGCCAAGGCACCACGGTCACCGTCTCCTCAGCCTCCACCAAGGGCCCATCGGTCT
AAACTGATGACCCCGGTTCCGTGGTGCCAGTGGCAGAGGAGTCGGAGGTGGTTCCCGGGTAGCCAGA
TCCCCCTGGCACCCTCCTCCAAGAGCAGGTCTGGGGGCACAGCGGCCCTGGGCTGCCTGGTCA
AGGGGGACCGTGGGAGGAGGTTCTCGTGGAGACCCCCGTGTCGCCGGGACCCGACGGACCAGT
AGGACTACTTCCCCGAACCGGTGACGGTGTCGTGGAACTCAGGCGCCCTGACCAGCGGCGTGCACAC
TCCTGATGAAGGGGCTTGGCCACTGCCACAGCACCTTGAGTCCGCGGGACTGGTCGCCGCACGTGTG
CTTCCCGGCTGTCCTACAGTCCTCAGGACTCTACTCCCTCAGCAGCGTGGTGACTGTGCCCTC
GAAGGGCCGACAGGATGTCAGGAGTCCTGAGATGAGGGAGTCGTCGCACCACTGACACGGGAG
CAGCAGCTTGGGCACCCAGACCTACATCTGCAACGTGAATCACAACCCCAGCAACACCAAGGTCGAC
GTCGTCGAACCCGTGGGTCTGGATGTAGACGTTGCACTTAGTGTTGGGGTCGTTGTGGTTCCAGCTG
AAGAAAGTTGAGCCCAAATCTTGTGACAAGACGCACACGTGCCCGCCGTGCCCGGCTCCGGAA
TTCTTTCAACTCGGGTTTAGAACACTGTTCTGCGTGTGCACGGGCGGCACGGGCCGAGGCCTT
CTGCTGGGTGGCCCGTAATAGCTAGCGTTAACATGCAAATTCTATTTCAAGGAGACAGTCATAATGA
GACGACCCACCGGGCATTATCGATCGCAATTGTACGTTTAAGATAAAGTTCCTCTGTCAGTATTACT
AATACCTATTGCCTACGGCAGCCGCTGGATTGTTATTACTCGCTGCCCAACCAGCGATGGCCG
TTATGGATAACGGATGCCGTCGGCGACCTAACAATAATGAGCGACGGGTTGGTCGCTACCGGC
ACATCGAGCTCTCCCAGTCTCCAGCAATCCTGTCTGCATCTCCAGGGGAGAAGGTCACAATGACTTG
TGTAGCTCGAGAGGGTCAGAGGTCGTTAGGACAGACGTAGAGGTCCCCTCTTCCAGTGTTACTGAAC
CAGGGCCAGCTCAAGTGTAACTTACATTCACTGGTACCAGCAGAAGCCAGGATCCTCCCCCAA
GTCCCGGTCGAGTTCACATTGAATGTAAGTGACCATGGTCGTCTTCGGTCCTAGGAGGGGTT
ATCCTGGATTTATGCCACATCCAACCTGGCTTCTGGAGTCCCTGCTCGCTTCAGTGGCAGTGGGTCT
TAGGACCTAAATACGGTGTAGGTTGGACCGAAGACCTCAGGGACGAGCGAAGTCACCGTCACCCAGA
GGGACCTCTTACTCTCTCACAATCAGCAGAGTGGAGGCTGAAGATGCTGCCACTTATTACTGC
CCCTGGAGAATGAGAGAGTGTTAGTCGTCTCACCTCCGACTTCTACGACGGTGAATAATGACG
CAACATTGGAGTAGTAAACCACCGACGTTCGGTGGAGGCACCAAGCTCGAGATCAAACGGACTGTGG
GTTGTAACCTCATCATTTGGTGGCTGCAAGCCACCTCCGTGGTTCGAGCTCTAGTTTGCCTGACACC
```

TABLE 20-continued

A5B7 F(ab')₂ sequences SEQ ID NOS: 31–32

```
CTGCACCATCTGTCTTCATCTTCCCGCCATCTGATGAGCAGTTGAAATCTGGAACTGCCTCTG
++++++++++|++++++++|++++++++|++++++++|++++++++|++++++++|++++|++++|+++
GACGTGGTAGACAGAAGTAGAAGGGCGGTAGACTACTCGTCAACTTTAGACCTTGACGGAGAC

TTGTGTGCCTGCTGAATAACTTCTATCCCAGAGAGGCCAAAGTACAGTGGAAGGTGGATAACGCCCT
++++++++++|++++++++|++++++++|++++++++|++++++++|++++++++|++++|++++|++++|++
AACACACGGACGACTTATTGAAGATAGGGTCTCTCCGGTTTCATGTCACCTTCCACCTATTGCGGGA

CCAATCGGGTAACTCCCAGGAGAGTGTCACAGAGCAGGACAGCAAGGACAGCACCTACAGCCT
++++++++++|++++++++|++++++++|++++++++|++++++++|++++++++|++++|++++|+++
GGTTAGCCCATTGAGGGTCCTCTCACAGTGTCTCGTCCTGTCGTTCCTGTCGTGGATGTCGGA

CAGCAGCACCCTGACGCTGAGCAAAGCAGACTACGAGAAACACAAAGTCTACGCCTGCGAAGTCACC
++++++++++|++++++++|++++++++|++++++++|++++++++|++++++++|++++|++++|++++|++
GTCGTCGTGGGACTGCGACTCGTTTCGTCTGATGCTCTTTGTGTTTCAGATGCGGACGCTTCAGTGG

CATCAGGGCCTGAGTTCGCCCGTCACAAAGAGCTTCAACCGCGGAGAGTGTTAGTAAGGATCC
++++++++++|++++++++|++++++++|++++++++|++++++++|++++++++|++++|++++|+++
GTAGTCCCGGACTCAAGCGGGCAGTGTTTCTCGAAGTTGGCGCCTCTCACAATCATTCCTAGG

AGCTCGAATTCCATCGATGATATCAGATCT
++++++++++|++++++++|++++++++|+++++++▶ 1590
TCGAGCTTAAGGTAGCTACTATAGTCTAGA
```

What is claimed is:

1. A T7 based promoter-driven protein expression system comprising a native operator sequence downstream of the T7 promoter sequence, and having a further operator sequence upstream of the T7 promoter sequence; wherein the system is a host cell transformed with a plasmid comprising the native operator sequence, the T7 promoter sequence, and the further operator sequence; wherein both the native operator sequence and the further operator sequence bind the lac repressor; and wherein the further operator sequence is a perfect palindrome operator (ppop) sequence.

2. A protein expression system as claimed in claim 1 wherein the native operator sequence downstream of the T7 promoter sequence is replaced by a ppop sequence that binds the lac repressor, so as to provide a tandem ppop operator.

3. A plasmid which comprises a target gene under T7 promoter control, and comprising a native operator sequence downstream of the T7 promoter sequence, and having a further operator sequence upstream of the T7 promoter sequence, wherein both the native operator sequence and the further operator sequence bind the lac repressor, and the further operator sequence is a perfect palindrome operator (ppop) sequence.

4. A plasmid as claimed in claim 3 wherein the native operator sequence downstream of the T7 promoter sequence is replaced by a ppop sequence that binds the lac repressor, so as to provide a tandem ppop sequence.

5. A plasmid selected from the group consisting of pZT7#3.0, pZT7#3.1, pZT7#3.2 and pZT7#3.3.

6. The plasmid pZT7#3.3.

7. A host cell transformed by a plasmid as claimed in any one of claims 3 and 4–6.

8. A host cell transformed by the plasmid pZT7#3.3.

9. An *E. Coli* cell transformed by the plasmid pZT7#3.3.

10. A method of producing a recombinant protein comprising:
   (a) transforming a host cell with a plasmid as recited in claim 1 which comprises a target gene that encodes a recombinant protein;
   (b) transcribing the target gene by addition of an inducing agent which relieves repression of the gene's transcription in the host cell, wherein the T7 promoter of the plasmid drives transcription of the target gene, such that a transcript encoding the recombinant protein is produced; and
   (c) translating the transcript to produce the recombinant protein.

11. A method of producing a recombinant protein comprising:
   (a) transforming a host cell with a plasmid as claimed in claim 3 which comprises a target gene that encodes a recombinant protein;
   (b) transcribing the target gene by addition of an inducing agent which relieves repression of the gene's transcription in the host cell, wherein the T7 promoter of the plasmid drives transcription of the target gene, such that a transcript encoding the recombinant protein is produced; and
   (c) translating the transcript to produce the recombinant protein.

12. A plasmid which comprises a T7 promoter sequence, an operator sequence downstream of the T7 promoter sequence, and having a further operator sequence upstream of the T7 promoter sequence, wherein both the operator sequence downstream of the T7 promotor sequence and the further operator sequence bind the lac repressor, and the further operator sequence is a perfect palindrome operator (ppop) sequence.

* * * * *

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 1:

GATGCTATAA TGCATGACAC CATCGAATGG CGCAA                35

(2) INFORMATION FOR SEQ ID NO: 2:

(i) SEQUENCE CHARACTERISTICS:
      (A) LENGTH: 41 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 2:

CAGTATGCAC AGTATGCATT TACATTAATT GCGTTGCGCT C          41

(2) INFORMATION FOR SEQ ID NO: 3:

(i) SEQUENCE CHARACTERISTICS:
      (A) LENGTH: 88 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 3:

AATTCCAGAC ATATGGTACC AGTACTCTAT ACTAGTTGAA GGATCCATGC CTCGAGAACG    60

CTGCAGAGCT AAGCTTGACA AGATCTAA    88

(2) INFORMATION FOR SEQ ID NO: 4:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

GATCTTAGAT CTTGTCAAGC TTAGCTCTGC AGCGTTCTCG AGGCATGGAT CCTTCAACTA    60

GTATAGAGTA CTGGTACCAT ATGTCTGG    88

(2) INFORMATION FOR SEQ ID NO: 5:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

AGCTTAACAA AGCCCGAAAG GAAGCTGAGT TGGCTGCTGC CACCGCTGAG CAATAACTAG    60

CATAACCCCT TGGGGCCTCT AAACGGGTCT TGAGGGGTTT TTTGA    105

(2) INFORMATION FOR SEQ ID NO: 6:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

GATCTCAAAA AACCCCTCAA GACCCGTTTA GAGGCCCCAA GGGGTTATGC TAGTTATTGC    60

TCAGCGGTGG CAGCAGCCAA CTCAGCTTCC TTTCGGGCTT TGTTA    105

(2) INFORMATION FOR SEQ ID NO: 7:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

TCGAGGCATT GTCCTCTTAG TTAAATGGAT ATAACGAGCC CCTCCTAAGG GCTAATTGCA    60

GGTTCGATTC CTGCAGGGGA CTCCACTGCA    90

(2) INFORMATION FOR SEQ ID NO: 8:

(i) SEQUENCE CHARACTERISTICS:
        (A) LENGTH: 82 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

GTGGAGTCCC CTGCAGGAAT CGAACCTGCA ATTAGCCCTT AGGAGGGGCT CGTTATATCC    60

ATTTAACTAA GAGGACAATG CC    82

(2) INFORMATION FOR SEQ ID NO: 9:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

CCTATTATAT TACTAATTAA TTGGGGACCC TAGAGGTCCC CTTTTTTATT TTAAAACCAT    60

GGAACCAACC G    71

(2) INFORMATION FOR SEQ ID NO: 10:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

AATTCGGTTG GTTCCATGGT TTTAAAATAA AAAGGGGAC CTCTAGGGTC CCCAATTAAT    60

TAGTAATATA ATAGG    75

(2) INFORMATION FOR SEQ ID NO: 11:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

AATTCCGAAA TTAATACGAC TCACTATAGG GGAATTGTGA GCGGATAACA ATTCCCCTCT    60

AGAAATAATT TGTTTAACT TTAAGAAGGA GATATACA    98

(2) INFORMATION FOR SEQ ID NO: 12:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

TATGTATATC TCCTTCTTAA AGTTAAACAA AATTATTTCT AGAGGGGAAT TGTTATCCGC    60

TCACAATTCC CCTATAGTGA GTCGTATTAA TTTCGG    96

(2) INFORMATION FOR SEQ ID NO: 13:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

```
AATTCCGAAA TTAATACGAC TCACTATAGG GGAATTGTGA GCGCTCACAA TTCCCCTCTA      60

GAAATAATTT TGTTTAACTT TAAGAAGGAG ATATACA                              97
```

(2) INFORMATION FOR SEQ ID NO: 14:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

```
TATGTATATC TCCTTCTTAA AGTTAAACAA AATTATTTCT AGAGGGGAAT TGTGAGCGCT      60

CACAATTCCC CTATAGTGAG TCGTATTAAT TTCGG                                95
```

(2) INFORMATION FOR SEQ ID NO: 15:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

```
CATGGACTGG TTAACAACCA ACCGGAATTG TGAGCGGATA ACAATTCCTC CAAGAACAAC      60

CATCCTAGCA ACACGGCGGT CCCCG                                           85
```

(2) INFORMATION FOR SEQ ID NO: 16:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

```
AATTCGGGGA CCGCCGTGTT GCTAGGATGG TTGTTCTTGG AGGAATTGTT ATCCGCTCAC      60

AATTCCGGTT GGTTGTTAAC ACGTC                                           85
```

(2) INFORMATION FOR SEQ ID NO: 17:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

```
CATGGACGTG TTAACAACCA ACCGGAATTG TGAGCGCTCA CAATTCCATC CAAGAACAAC      60

CATCCTAGCA ACACGGCGGT CCCCG                                            85
```

(2) INFORMATION FOR SEQ ID NO: 18:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

```
AATTCGGGGA CCGCCGTGTT GCTAGGATGG TTGTTCTTGG ATGGAATTGT GAGCGCTCAC      60

AATTCCGGTT GGTTGTTAAC ACGTC                                            85
```

(2) INFORMATION FOR SEQ ID NO: 19:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

```
CATATGGTAC GTAGCTCCTC TCGCACTCCG TCCGATAAGC CGGTTGCTCA TGTAGTTGCT      60

AACCCTCAGG CAGAAGGTCA GCTGCAGTGG CTGAACCGTC GCGCTAACGC CCTGCTGGCA     120

AACGGCGTTG AGCTCCGTGA TAACCAGCTC GTGGTACCTT CTGAAGGTCT GTACCTGATC     180

TATTCTCAAG TACTGTTCAA GGGTCAGGGC TGCCCGTCGA CTCATGTTCT GCTGACTCAC     240

ACCATCAGCC GTATTGCTGT ATCTTACCAG ACCAAAGTTA ACCTGCTGAG CGCTATCAAG     300

TCTCCGTGCC AGCGTGAAAC TCCCGAGGGT GCAGAAGCGA AACCATGGTA TGAACCGATC     360

TACCTGGGTG GCGTATTTCA ACTGGAGAAA GGTGACCGTC TGTCCGCAGA AATCAACCGT     420

CCTGACTATC TAGATTTCGC TGAATCTGGC CAGGTGTACT TCGGTATTAT CGCACTGTAA     480

TAATAAGGAT CC                                                         492
```

(2) INFORMATION FOR SEQ ID NO: 20:

(i) SEQUENCE CHARACTERISTICS:
        (A) LENGTH: 492 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

```
GGATCCTTAT TATTACAGTG CGATAATACC GAAGTACACC TGGCCAGATT CAGCGAAATC      60

TAGATAGTCA GGACGGTTGA TTTCTGCGGA CAGACGGTCA CCTTTCTCCA GTTGAAATAC     120

GCCACCCAGG TAGATCGGTT CATACCATGG TTTCGCTTCT GCACCCTCGG GAGTTTCACG     180

CTGGCACGGA GACTTGATAG CGCTCAGCAG GTTAACTTTG GTCTGGTAAG ATACAGCAAT     240

ACGGCTGATG GTGTGAGTCA GCAGAACATG AGTCGACGGG CAGCCCTGAC CCTTGAACAG     300

TACTTGAGAA TAGATCAGGT ACAGACCTTC AGAAGGTACC ACGAGCTGGT TATCACGGAG     360
```

```
CTCAACGCCG TTTGCCAGCA GGGCGTTAGC GCGACGGTTC AGCCACTGCA GCTGACCTTC      420

TGCCTGAGGG TTAGCAACTA CATGAGCAAC CGGCTTATCG GACGGAGTGC GAGAGGAGCT      480

ACGTACCATA TG                                                         492
```

(2) INFORMATION FOR SEQ ID NO: 21:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

```
CATATGCCCG CGGCGCACCT GCCCTTCTTC TACGGCAGCA TCTCGCGTGC CGAGGCCGAG       60

GAGCACCTGA AGCTGGCGGG CATGGCGGAC GGGCTCTTCC TGCTGCGCCA GTGCCTGCGC      120

TCGCTGGGCG GCTATGTGCT GTCGCTCGTG CACGATGTGC GCTTCCACCA CTTTCCCATC      180

GAGCGCCAGC TCAACGGCAC CTACGCCATT GCCGGCGGCA AAGCGCACTG TGGACCGGCA      240

GAGCTCTGCG AGTTCTACTC GCGCGACCCC GACGGGCTGC CCTGCAACCT GCGCAAGCCG      300

TGCAACCGGC CGTCGGGCCT CGAGCCGCAG CCGGGGGTCT TCGACTGCCT GCGAGACGCC      360

ATGGTGCGTG ACTACGTGCG CCAGACGTGG AAGCTGGAGG GCGAGGCCCT GGAGCAGGCC      420

ATCATCAGCC AGGCCCCGCA GGTGGAGAAG CTCATTGCTA CGACGGCCCA CGAGCGGATG      480

CCCTGGTACC ACAGCAGCCT GACGCGTGAG GAGGCCGAGC GCAAACTTTA CTCTGGGGCG      540

CAGACCGACG GCAAGTTCCT GCTGAGGCCG CGGAAGGAGC AGGGCACATA CGCCCTGTCC      600

CTCATCTATG GAAGACGGT GTACCACTAC CTCATCAGCC AAGACAAGGC GGGCAAGTAC      660

TGCATTCCCG AGGGCACCAA GTTTGACACG CTCTGGCAGC TGGTGGAGTA TCTGAAGCTG      720

AAGGCGGACG GGCTCATCTA CTGCCTGAAG GAGGCCTGCC CAACAGCAG TGCCAGCCAT      780

CACCATCACC ATCACTAATA AAGATCT                                         807
```

(2) INFORMATION FOR SEQ ID NO: 22:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

```
AGATCTTTAT TAGTGATGGT GATGGTGATG GCTGGCACTG CTGTTGGGGC AGGCCTCCTT       60

CAGGCAGTAG ATGAGCCCGT CCGCCTTCAG CTTCAGATAC TCCACCAGCT GCCAGAGCGT      120

GTCAAACTTG GTGCCCTCGG GAATGCAGTA CTTGCCCGCC TTGTCTTGGC TGATGAGGTA      180

GTGGTACACC GTCTTCCCAT AGATGAGGGA CAGGGCGTAT GTGCCCTGCT CCTTCCGCGG      240

CCTCAGCAGG AACTTGCCGT CGGTCTGCGC CCCAGAGTAA AGTTTGCGCT CGGCCTCCTC      300

ACGCGTCAGG CTGCTGTGGT ACCAGGGCAT CCGCTCGTGG GCCGTCGTAG CAATGAGCTT      360

CTCCACCTGC GGGGCCTGGC TGATGATGGC CTGCTCCAGG GCCTCGCCCT CCAGCTTCCA      420

CGTCTGGCGC ACGTAGTCAC GCACCATGGC GTCTCGCAGG CAGTCGAAGA CCCCCGGCTG      480

CGGCTCGAGG CCCGACGGCC GGTTGCACGG CTTGCGCAGG TTGCAGGGCA GCCCGTCGGG      540
```

| | |
|---|---|
| GTCGCGCGAG TAGAACTCGC AGAGCTCTGC CGGTCCACAG TGCGCTTTGC CGCCGGCAAT | 600 |
| GGCGTAGGTG CCGTTGAGCT GGCGCTCGAT GGGAAAGTGG TGGAAGCGCA CATCGTGCAC | 660 |
| GAGCGACAGC ACATAGCCGC CCAGCGAGCG CAGGCACTGG CGCAGCAGGA AGAGCCCGTC | 720 |
| CGCCATGCCC GCCAGCTTCA GGTGCTCCTC GGCCTCGGCA CGCGAGATGC TGCCGTAGAA | 780 |
| GAAGGGCAGG TGCGCCGCGG GCATATG | 807 |

(2) INFORMATION FOR SEQ ID NO: 23:

(i) SEQUENCE CHARACTERISTICS:
        (A) LENGTH: 1029 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

| | |
|---|---|
| CATATGGTAC CAACCCACTC TCCGTCCTCT AAGGATGAGC AGTCGATCGG ACTGAAGGAC | 60 |
| TCCTTGCTGG CCCACTCCTC TGACCCTGTG GAGATGCGGA GGCTCAACTA CCAGACCCCA | 120 |
| GGTATGCGAG ACCACCCACC CATCCCCATC ACCGACCTGG CGGACAACAT CGAGCGCCTC | 180 |
| AAAGCCAACG ATGGCCTCAA GTTCTCCCAG GAGTATGAGT CCATCGACCC TGGACAGCAG | 240 |
| TTCACGTGGG AGAATTCAAA CCTGGAGGTG AACAAGCCCA AGAACCGCTA TGCGAATGTC | 300 |
| ATCGCCTACG ACCACTCTCG AGTCATCCTT ACCTCTATCG ATGGCGTCCC CGGGAGTGAC | 360 |
| TACATCAATG CCAACTACAT CGATGGCTAC CGCAAGCAGA ATGCCTACAT CGCCACGCAG | 420 |
| GGCCCCCTGC CCGAGACCAT GGGCGATTTC TGGAGAATGG TGTGGGAACA GCGCACGGCC | 480 |
| ACTGTGGTCA TGATGACACG GCTGGAGGAG AAGTCCCGGG TAAAATGTGA TCAGTACTGG | 540 |
| CCAGCCCGTG GCACCGAGAC CTGTGGCCTT ATTCAGGTGA CCCTGTTGGA CACAGTGGAG | 600 |
| CTGGCCACAT ACACTGTGCG CACCTTCGCA CTCCACAAGA GTGGCTCCAG TGAGAAGCGT | 660 |
| GAGCTGCGTC AGTTTCAGTT CATGGCCTGG CCAGACCATG GAGTTCCTGA GTACCCAACT | 720 |
| CCCATCCTGG CCTTCCTACG ACGGGTCAAG GCCTGCAACC CCCTAGACGC AGGGCCCATG | 780 |
| GTGGTGCACT GCAGCGCGGG CGTGGGCCGC ACCGGCTGCT TCATCGTGAT TGATGCCATG | 840 |
| TTGGAGCGGA TGAAGCACGA GAAGACGGTG GACATCTATG GCCACGTGAC CTGCATGCGA | 900 |
| TCACAGAGGA ACTACATGGT GCAGACGGAG GACCAGTACG TGTTCATCCA TGAGGCGCTG | 960 |
| CTGGAGGCTG CCACGTGCGG CCACACAGAG GTGCCTGCCC GCAACCTGTA TGCCCACTAA | 1020 |
| TGAAGATCT | 1029 |

(2) INFORMATION FOR SEQ ID NO: 24:

(i) SEQUENCE CHARACTERISTICS:
        (A) LENGTH: 1029 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 24:

| | |
|---|---|
| AGATCTTCAT TAGTGGGCAT ACAGGTTGCG GGCAGGCACC TCTGTGTGGC CGCACGTGGC | 60 |
| AGCCTCCAGC AGCGCCTCAT GGATGAACAC GTACTGGTCC TCCGTCTGCA CCATGTAGTT | 120 |
| CCTCTGTGAT CGCATGCAGG TCACGTGGCC ATAGATGTCC ACCGTCTTCT CGTGCTTCAT | 180 |
| CCGCTCCAAC ATGGCATCAA TCACGATGAA GCAGCCGGTG CGGCCCACGC CCGCGCTGCA | 240 |

```
GTGCACCACC ATGGGCCCTG CGTCTAGGGG GTTGCAGGCC TTGACCCGTC GTAGGAAGGC        300

CAGGATGGGA GTTGGGTACT CAGGAACTCC ATGGTCTGGC CAGGCCATGA ACTGAAACTG        360

ACGCAGCTCA CGCTTCTCAC TGGAGCCACT CTTGTGGAGT GCGAAGGTGC GCACAGTGTA        420

TGTGGCCAGC TCCACTGTGT CCAACAGGGT CACCTGAATA AGGCCACAGG TCTCGGTGCC        480

ACGGGCTGGC CAGTACTGAT CACATTTTAC CCGGGACTTC TCCTCCAGCC GTGTCATCAT        540

GACCACAGTG GCCGTGCGCT GTTCCCACAC CATTCTCCAG AAATCGCCCA TGGTCTCGGG        600

CAGGGGGCCC TGCGTGGCGA TGTAGGCATT CTGCTTGCGG TAGCCATCGA TGTAGTTGGC        660

ATTGATGTAG TCACTCCCGG GGACGCCATC GATAGAGGTA AGGATGACTC GAGAGTGGTC        720

GTAGGCGATG ACATTCGCAT AGCGGTTCTT GGGCTTGTTC ACCTCCAGGT TTGAATTCTC        780

CCACGTGAAC TGCTGTCCAG GGTCGATGGA CTCATACTCC TGGGAGAACT TGAGGCCATC        840

GTTGGCTTTG AGGCGCTCGA TGTTGTCCGC CAGGTCGGTG ATGGGGATGG GTGGGTGGTC        900

TCGCATACCT GGGGTCTGGT AGTTGAGCCT CCGCATCTCC ACAGGGTCAG AGGAGTGGGC        960

CAGCAAGGAG TCCTTCAGTC CGATCGACTG CTCATCCTTA GAGGACGGAG AGTGGGTTGG       1020

TACCATATG                                                               1029

(2) INFORMATION FOR SEQ ID NO: 25:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 25:

CATATGCTTA AGATCGCTGC TTTCAACATA CGTACCTTCG GTGAATCTAA AATGTCTAAC         60

GCTACGCTAG CATCTTACAT CGTACGCATC GTACGCCGTT ACGATATCGT TCTGATCCAG        120

GAAGTTCGCG ACTCTCACCT GGTTGCAGTT GGTAAACTTC TAGACTACCT GAACCAGGAC        180

GACCCGAACA CCTACCACTA CGTTGTTTCT GAACCCCTCG GCGTAACTC TTACAAAGAA        240

CGGTACCTGT TCCTGTTCCG TCCGAACAAA GTTTCAGTAC TGGATACCTA CCAGTACGAC        300

GACGGATGCG AATCTTGCGG TAACGACTCT TTCTCCCGGG AACCGGCTGT TGTTAAATTC        360

TCGAGCCACT CTACCAAGGT TAAAGAGTTC GCTATCGTTG CTCTGCACAG CGCGCCGTCT        420

GACGCTGTTG CTGAAATCAA CTCTCTGTAC GACGTTTACC TGGACGTTCA GCAGAAATGG        480

CACCTGAACG ACGTCATGCT GATGGGTGAC TTCAACGCTG ACTGCTCTTA TGTAACCTCT        540

TCTCAGTGGT CATCGATTCG TCTGCGCACC TCGTCGACCT TCCAGTGGCT GATCCCGGAC        600

TCCGCTGACA CCACCGCTAC TAGTACCAAC TGCGCTTACG ACCGTATCGT TGTTGCTGGA        660

TCCCTGCTGC AGTCTTCTGT TGTACCGGGT AGCGCGGCCC CGTTCGACTT CCAGGCTGCG        720

TATGGTCTTT CGAACGAAAT GGCGCTGGCC ATCTCTGATC ACTACCCGGT TGAGGTTACC        780

CTGACCTAAT AGAGATCT                                                     798

(2) INFORMATION FOR SEQ ID NO: 26:

(i) SEQUENCE CHARACTERISTICS:
        (A) LENGTH: 798 base pairs
        (B) TYPE: nucleic acid
        (C) STRANDEDNESS: single
        (D) TOPOLOGY: linear
```

(ii) MOLECULE TYPE: other nucleic acid (xi) SEQUENCE DESCRIPTION: SEQ ID NO: 26:

| | | | | | |
|---|---|---|---|---|---|
| AGATCTCTAT | TAGGTCAGGG | TAACCTCAAC | CGGGTAGTGA | TCAGAGATGG | CCAGCGCCAT | 60 |
| TTCGTTCGAA | AGACCATACG | CAGCCTGGAA | GTCGAACGGG | GCCGCGCTAC | CCGGTACAAC | 120 |
| AGAAGACTGC | AGCAGGGATC | CAGCAACAAC | GATACGGTCG | TAAGCGCAGT | TGGTACTAGT | 180 |
| AGCGGTGGTG | TCAGCGGAGT | CCGGGATCAG | CCACTGGAAG | GTCGACGAGG | TGCGCAGACG | 240 |
| AATCGATGAC | CACTGAGAAG | AGGTTACATA | AGAGCAGTCA | GCGTTGAAGT | CACCCATCAG | 300 |
| CATGACGTCG | TTCAGGTGCC | ATTTCTGCTG | AACGTCCAGG | TAAACGTCGT | ACAGAGAGTT | 360 |
| GATTTCAGCA | ACAGCGTCAG | ACGGCGCGCT | GTGCAGAGCA | ACGATAGCGA | ACTCTTTAAC | 420 |
| CTTGGTAGAG | TGGCTCGAGA | ATTTAACAAC | AGCCGGTTCC | CGGGAGAAAG | AGTCGTTACC | 480 |
| GCAAGATTCG | CATCCGTCGT | CGTACTGGTA | GGTATCCAGT | ACTGAAACTT | TGTTCGGACG | 540 |
| GAACAGGAAC | AGGTACCGTT | CTTTGTAAGA | GTTACGCCCG | AGGGGTTCAG | AAACAACGTA | 600 |
| GTGGTAGGTG | TTCGGGTCGT | CCTGGTTCAG | GTAGTCTAGA | AGTTTACCAA | CTGCAACCAG | 660 |
| GTGAGAGTCG | CGAACTTCCT | GGATCAGAAC | GATATCGTAA | CGGCGTACGA | TGCGTACGAT | 720 |
| GTAAGATGCT | AGCGTAGCGT | TAGACATTTT | AGATTCACCG | AAGGTACGTA | TGTTGAAAGC | 780 |
| AGCGATCTTA | AGCATATG | | | | | 798 |

(2) INFORMATION FOR SEQ ID NO: 27:

(i) SEQUENCE CHARACTERISTICS:
        (A) LENGTH: 1053 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 27:

| | | | | | |
|---|---|---|---|---|---|
| ATGAAATACC | TATTGCCTAC | GGCAGCCGCT | GGATTGTTAT | TACTCGCTGC | CCAACCAGCC | 60 |
| ATGGCGGCAA | CTGGTCACTC | TTACGAGAAG | TACAACAAGT | GGGAAACGAT | AGAGGCTTGG | 120 |
| ACTCAACAAG | TCGCCACTGA | GAATCCAGCC | CTCATCTCTC | GCAGTGTTAT | CGGAACCACA | 180 |
| TTTGAGGGAC | GCGCTATTTA | CCTCCTGAAG | GTTGGCAAAG | CTGGACAAAA | TAAGCCTGCC | 240 |
| ATTTTCATGG | ACTGTGGTTT | CCATGCCAGA | GAGTGGATTT | CTCCTGCATT | CTGCCAGTGG | 300 |
| TTTGTAAGAG | AGGCTGTTCG | TACCTATGGA | CGTGAGATCC | AAGTGACAGA | GCTTCTCGAC | 360 |
| AAGTTAGACT | TTTATGTCCT | GCCTGTGCTC | AATATTGATG | GCTACATCTA | CACCTGGACC | 420 |
| AAGAGCCGAT | TTTGGAGAAA | GACTCGCTCC | ACCCATACTG | GATCTAGCTG | CATTGGCACA | 480 |
| GACCCCAACA | GAAATTTTGA | TGCTGGTTGG | TGTGAAATTG | GAGCCTCTCG | AAACCCCTGT | 540 |
| GATGAAACTT | ACTGTGGACC | TGCCGCAGAG | TCTGAAAAGG | AGACCAAGGC | CCTGGCTGAT | 600 |
| TTCATCCGCA | ACAAACTCTC | TTCCATCAAG | GCATATCTGA | CAATCCACTC | GTACTCCCAA | 660 |
| ATGATGATCT | ACCCTTACTC | ATATGCTTAC | AAACTCGGTG | AGAACAATGC | TGAGTTGAAT | 720 |
| GCCCTGGCTA | AAGCTACTGT | GAAAGAACTT | GCCTCACTGC | ACGGCACCAA | GTACACATAT | 780 |
| GGCCCGGGAG | CTACAACAAT | CTATCCTGCT | GCTGGGGGCT | CTAAAGACTG | GCTTATGAC | 840 |
| CAAGGAATCA | GATATTCCTT | CACCTTTGAA | CTTCGAGATA | CAGGCAGATA | TGGCTTTCTC | 900 |
| CTTCCAGAAT | CCCAGATCCG | GGCTACCTGC | GAGGAGACCT | TCCTGGCAAT | CAAGTATGTT | 960 |
| GCCAGCTACG | TCCTGGAACA | CCTGTACCAC | CACCATCACC | ACCATGAGTT | CGAGGAGCAG | 1020 |

```
AAGCTGATCT CTGAGGAGGA CCTGAACTAA TAA                                  1053
```

(2) INFORMATION FOR SEQ ID NO: 28:

(i) SEQUENCE CHARACTERISTICS:
        (A) LENGTH: 1053 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 28:

```
TTATTAGTTC AGGTCCTCCT CAGAGATCAG CTTCTGCTCC TCGAACTCAT GGTGGTGATG      60
GTGGTGGTAC AGGTGTTCCA GGACGTAGCT GGCAACATAC TTGATTGCCA GGAAGGTCTC     120
CTCGCAGGTA GCCCGGATCT GGGATTCTGG AAGGAGAAAG CCATATCTGC CTGTATCTCG     180
AAGTTCAAAG GTGAAGGAAT ATCTGATTCC TTGGTCATAA GCCCAGTCTT TAGAGCCCCC     240
AGCAGCAGGA TAGATTGTTG TAGCTCCCGG GCCATATGTG TACTTGGTGC CGTGCAGTGA     300
GGCAAGTTCT TTCACAGTAG CTTTAGCCAG GGCATTCAAC TCAGCATTGT TCTCACCGAG     360
TTTGTAAGCA TATGAGTAAG GGTAGATCAT CATTTGGGAG TACGAGTGGA TTGTCAGATA     420
TGCCTTGATG GAAGAGAGTT TGTTGCGGAT GAAATCAGCC AGGGCCTTGG TCTCCTTTTC     480
AGACTCTGCG GCAGGTCCAC AGTAAGTTTC ATCACAGGGG TTTCGAGAGG CTCCAATTTC     540
ACACCAACCA GCATCAAAAT TTCTGTTGGG GTCTGTGCCA ATGCAGCTAG ATCCAGTATG     600
GGTGGAGCGA GTCTTTCTCC AAAATCGGCT CTTGGTCCAG GTGTAGATGT AGCCATCAAT     660
ATTGAGCACA GGCAGGACAT AAAAGTCTAA CTTGTCGAGA AGCTCTGTCA CTTGGATCTC     720
ACGTCCATAG GTACGAACAG CCTCTCTTAC AAACCACTGG CAGAATGCAG GAGAAATCCA     780
CTCTCTGGCA TGGAAACCAC AGTCCATGAA ATGGCAGGTT TATTTTGTC CAGCTTTGCC      840
AACCTTCAGG AGGTAAATAG CGCGTCCCTC AAATGTGGTT CCGATAACAC TGCGAGAGAT     900
GAGGGCTGGA TTCTCAGTGG CGACTTGTTG AGTCCAAGCC TCTATCGTTT CCCACTTGTT     960
GTACTTCTCG TAAGAGTGAC CAGTTGCCGC CATGGCTGGT TGGGCAGCGA GTAATAACAA    1020
TCCAGCGGCT GCCGTAGGCA ATAGGTATTT CAT                                 1053
```

(2) INFORMATION FOR SEQ ID NO: 29:

(i) SEQUENCE CHARACTERISTICS:
        (A) LENGTH: 213 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 29:

```
ATGGTTACCT GCTGTTATAA CTTCACCAAC CGTAAAATCT CAGTGCAGAG GCTCGCGAGC      60
TATAGAAGAA TCACCAGCAG CAAGTGTCCC AAAGAAGCTG TGATCTTCAA GACCATTGTG     120
GCCAAGGAGA TCTGTGCTGA CCCCAAGCAG AAGTGGGTTC AGGATTCCAT GGACCACCTG     180
GACAAGCAAA CCCAAACTCC GAAGACTTGA TGA                                  213
```

(2) INFORMATION FOR SEQ ID NO: 30:

(i) SEQUENCE CHARACTERISTICS:
        (A) LENGTH: 213 base pairs
        (B) TYPE: nucleic acid
        (C) STRANDEDNESS: single (D) TOPOLOGY: linear (ii) MOLECULE TYPE: other nucleic acid (xi) SEQUENCE DESCRIPTION: SEQ ID NO: 30:

| | | |
|---|---|---|
| TCATCAAGTC TTCGGAGTTT GGGTTTGCTT GTCCAGGTGG TCCATGGAAT CCTGAACCCA | 60 |
| CTTCTGCTTG GGGTCAGCAC AGATCTCCTT GGCCACAATG GTCTTGAAGA TCACAGCTTC | 120 |
| TTTGGGACAC TTGCTGCTGG TGATTCTTCT ATAGCTCGCG AGCCTCTGCA CTGAGATTTT | 180 |
| ACGGTTGGTG AAGTTATAAC AGCAGGTAAC CAT | 213 |

(2) INFORMATION FOR SEQ ID NO: 31:

(i) SEQUENCE CHARACTERISTICS:
      (A) LENGTH: 1590 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO: 31:

| | |
|---|---|
| CATATGAAAT ACCTATTGCC TACGGCAGCC GCTGGATTGT TATTACTCGC TGCCCAACCA | 60 |
| GCGATGGCCC AGGTGCAGCT GCAGGAATCT GGTGGTGGCT TAGTTCAACC TGGTGGTTCC | 120 |
| CTGAGACTCT CCTGTGCAAC TTCTGGGTTC ACCTTCACTG ATTACTACAT GAACTGGGTC | 180 |
| CGCCAGCCTC CAGGAAAGGC ACTTGAGTGG TTGGGTTTTA TTGGAAACAA AGCTAATGGT | 240 |
| TACACAACAG AGTACAGTGC ATCTGTGAAG GGTCGGTTCA CCATCTCCAG AGATAAATCC | 300 |
| CAAAGCATCC TCTATCTTCA AATGAACACC CTGAGAGCTG AGGACAGTGC CACTTATTAC | 360 |
| TGTACAAGAG ATAGGGGGCT ACGGTTCTAC TTTGACTACT GGGGCCAAGG CACCACGGTC | 420 |
| ACCGTCTCCT CAGCCTCCAC CAAGGGCCCA TCGGTCTTCC CCCTGGCACC CTCCTCCAAG | 480 |
| AGCACCTCTG GGGGCACAGC GGCCCTGGGC TGCCTGGTCA AGGACTACTT CCCCGAACCG | 540 |
| GTGACGGTGT CGTGGAACTC AGGCGCCCTG ACCAGCGGCG TGCACACCTT CCCGGCTGTC | 600 |
| CTACAGTCCT CAGGACTCTA CTCCCTCAGC AGCGTGGTGA CTGTGCCCTC CAGCAGCTTG | 660 |
| GGCACCCAGA CCTACATCTG CAACGTGAAT CACAACCCCA GCAACACCAA GGTCGACAAG | 720 |
| AAAGTTGAGC CCAAATCTTG TGACAAGACG CACACGTGCC CGCCGTGCCC GGCTCCGGAA | 780 |
| CTGCTGGGTG GCCCGTAATA GCTAGCGTTA ACATGCAAAT TCTATTTCAA GGAGACAGTC | 840 |
| ATAATGAAAT ACCTATTGCC TACGGCAGCC GCTGGATTGT TATTACTCGC TGCCCAACCA | 900 |
| GCGATGGCCG ACATCGAGCT CTCCCAGTCT CCAGCAATCC TGTCTGCATC TCCAGGGGAG | 960 |
| AAGGTCACAA TGACTTGCAG GGCCAGCTCA AGTGTAACTT ACATTCACTG GTACCAGCAG | 1020 |
| AAGCCAGGAT CCTCCCCCAA ATCCTGGATT TATGCCACAT CCAACCTGGC TTCTGGAGTC | 1080 |
| CCTGCTCGCT TCAGTGGCAG TGGGTCTGGG ACCTCTTACT CTCTCACAAT CAGCAGAGTG | 1140 |
| GAGGCTGAAG ATGCTGCCAC TTATTACTGC CAACATTGGA GTAGTAAACC ACCGACGTTC | 1200 |
| GGTGGAGGCA CCAAGCTCGA GATCAAACGG ACTGTGGCTG CACCATCTGT CTTCATCTTC | 1260 |
| CCGCCATCTG ATGAGCAGTT GAAATCTGGA ACTGCCTCTG TTGTGTGCCT GCTGAATAAC | 1320 |
| TTCTATCCCA GAGAGGCCAA AGTACAGTGG AAGGTGGATA ACGCCCTCCA ATCGGGTAAC | 1380 |
| TCCCAGGAGA GTGTCACAGA GCAGGACAGC AAGGACAGCA CCTACAGCCT CAGCAGCACC | 1440 |
| CTGACGCTGA GCAAAGCAGA CTACGAGAAA CACAAAGTCT ACGCCTGCGA AGTCACCCAT | 1500 |
| CAGGGCCTGA GTTCGCCCGT CACAAAGAGC TTCAACCGCG GAGAGTGTTA GTAAGGATCC | 1560 |

```
AGCTCGAATT CCATCGATGA TATCAGATCT                                1590
```

(2) INFORMATION FOR SEQ ID NO: 32:

(i) SEQUENCE CHARACTERISTICS:
        (A) LENGTH: 1590 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 32:

```
AGATCTGATA TCATCGATGG AATTCGAGCT GGATCCTTAC TAACACTCTC CGCGGTTGAA    60
GCTCTTTGTG ACGGGCGAAC TCAGGCCCTG ATGGGTGACT TCGCAGGCGT AGACTTTGTG   120
TTTCTCGTAG TCTGCTTTGC TCAGCGTCAG GGTGCTGCTG AGGCTGTAGG TGCTGTCCTT   180
GCTGTCCTGC TCTGTGACAC TCTCCTGGGA GTTACCCGAT TGGAGGGCGT TATCCACCTT   240
CCACTGTACT TTGGCCTCTC TGGGATAGAA GTTATTCAGC AGGCACACAA CAGAGGCAGT   300
TCCAGATTTC AACTGCTCAT CAGATGGCGG GAAGATGAAG ACAGATGGTG CAGCCACAGT   360
CCGTTTGATC TCGAGCTTGG TGCCTCCACC GAACGTCGGT GGTTTACTAC TCCAATGTTG   420
GCAGTAATAA GTGGCAGCAT CTTCAGCCTC CACTCTGCTG ATTGTGAGAG AGTAAGAGGT   480
CCCAGACCCA CTGCCACTGA AGCGAGCAGG GACTCCAGAA GCCAGGTTGG ATGTGGCATA   540
AATCCAGGAT TTGGGGGAGG ATCCTGGCTT CTGCTGGTAC CAGTGAATGT AAGTTACACT   600
TGAGCTGGCC CTGCAAGTCA TTGTGACCTT CTCCCCTGGA GATGCAGACA GGATTGCTGG   660
AGACTGGGAG AGCTCGATGT CGGCCATCGC TGGTTGGGCA GCGAGTAATA ACAATCCAGC   720
GGCTGCCGTA GGCAATAGGT ATTTCATTAT GACTGTCTCC TTGAAATAGA ATTTGCATGT   780
TAACGCTAGC TATTACGGGC CACCCAGCAG TTCCGGAGCC GGGCACGGCG GGCACGTGTG   840
CGTCTTGTCA CAAGATTTGG GCTCAACTTT CTTGTCGACC TTGGTGTTGC TGGGGTTGTG   900
ATTCACGTTG CAGATGTAGG TCTGGGTGCC CAAGCTGCTG GAGGGCACAG TCACCACGCT   960
GCTGAGGGAG TAGAGTCCTG AGGACTGTAG GACAGCCGGG AAGGTGTGCA CGCCGCTGGT  1020
CAGGGCGCCT GAGTTCCACG ACACCGTCAC CGGTTCGGGG AAGTAGTCCT TGACCAGGCA  1080
GCCCAGGGCC GCTGTGCCCC CAGAGGTGCT CTTGGAGGAG GGTGCCAGGG GGAAGACCGA  1140
TGGGCCCTTG GTGGAGGCTG AGGAGACGGT GACCGTGGTG CCTTGGCCCC AGTAGTCAAA  1200
GTAGAACCGT AGCCCCCTAT CTCTTGTACA GTAATAAGTG GCACTGTCCT CAGCTCTCAG  1260
GGTGTTCATT TGAAGATAGA GGATGCTTTG GGATTTATCT CTGGAGATGG TGAACCGACC  1320
CTTCACAGAT GCACTGTACT CTGTTGTGTA ACCATTAGCT TTGTTTCCAA TAAAACCCAA  1380
CCACTCAAGT GCCTTTCCTG GAGGCTGGCG GACCCAGTTC ATGTAGTAAT CAGTGAAGGT  1440
GAACCCAGAA GTTGCACAGG AGAGTCTCAG GGAACCACCA GGTTGAACTA AGCCACCACC  1500
AGATTCCTGC AGCTGCACCT GGGCCATCGC TGGTTGGGCA GCGAGTAATA ACAATCCAGC  1560
GGCTGCCGTA GGCAATAGGT ATTTCATATG                                  1590
```